(12) United States Patent
Liebler et al.

(10) Patent No.: US 11,204,355 B2
(45) Date of Patent: Dec. 21, 2021

(54) IMMUNE CHECKPOINT MOLECULAR FITNESS PROFILING BY MASS SPECTROMETRY

(71) Applicant: Vanderbilt University, Nashville, TN (US)

(72) Inventors: Daniel C. Liebler, Brentwood, TN (US); Lisa J. Zimmerman, Franklin, TN (US); Hyoungjoo Lee, Brentwood, TN (US); Carlos A. Morales Betanzos, Brentwood, TN (US); Douglas B. Johnson, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 977 days.

(21) Appl. No.: 15/899,970

(22) Filed: Feb. 20, 2018

(65) Prior Publication Data

US 2018/0238904 A1 Aug. 23, 2018

Related U.S. Application Data

(60) Provisional application No. 62/461,092, filed on Feb. 20, 2017.

(51) Int. Cl.
| | | |
|---|---|---|
| *G01N 33/68* | (2006.01) | |
| *C07K 16/28* | (2006.01) | |
| *A61P 35/00* | (2006.01) | |
| *G01N 33/574* | (2006.01) | |

(52) U.S. Cl.
CPC .......... *G01N 33/6893* (2013.01); *A61P 35/00* (2018.01); *C07K 16/2818* (2013.01); *C07K 16/2827* (2013.01); *G01N 33/57492* (2013.01); *G01N 33/6848* (2013.01); *G01N 2333/70521* (2013.01); *G01N 2333/70532* (2013.01); *G01N 2800/52* (2013.01)

(58) Field of Classification Search
CPC ......... G01N 33/6893; G01N 33/57492; G01N 33/6848; A61P 35/00; C07K 16/2818; C07K 16/2827
USPC ........................................................ 702/19
See application file for complete search history.

(56) References Cited

U.S. PATENT DOCUMENTS

| | | |
|---|---|---|
| 6,174,293 B1 | 1/2001 | Buck et al. |
| 2007/0019854 A1 | 1/2007 | Gholap et al. |
| 2008/0226554 A1 | 9/2008 | Colgan et al. |
| 2008/0312260 A1 | 12/2008 | Haley et al. |
| 2011/0306514 A1 | 12/2011 | Hewitt et al. |
| 2014/0234854 A1 | 8/2014 | Blume et al. |
| 2016/0313343 A1 | 10/2016 | Krizman et al. |

FOREIGN PATENT DOCUMENTS

| | | |
|---|---|---|
| EP | 2309262 A1 | 4/2011 |
| JP | 2010533836 A | 10/2010 |
| JP | 2012515334 A | 7/2012 |
| WO | WO2013165598 | 11/2013 |

OTHER PUBLICATIONS

Abbatiello et al., "Design, implementation and multisite evaluation of a system suitability protocol for the quantitative assessment of instrument performance in liquid chromatography-multiple reaction monitoring-MS (LC-MRM-MS)," Mol Cell Proteomics, 2013; 12: 2623-2639.

Abbatiello et al., "Large-Scale Interlaboratory Study to Develop, Analytically Validate and Apply Highly Multiplexed, Quantitative Peptide Assays to Measure Cancer-Relevant Proteins in Plasma," Mol Cell Proteomics 2015; 14: 2357-2374.

Addona et al., "Multi-site assessment of the precision and reproducibility of multiple reaction monitoring-based measurements of proteins in plasma," Nat Biotechnol. Jul. 2009;27(7):633-41.

Anderson, "Tim-3: an emerging target in the cancer immunotherapy landscape," Cancer Immunol Res., 2014; 2: 393-398.

Bassani-Sternberg et al., "Mass spectrometry-based antigen discovery for cancer immunotherapy," Curr Opin Immunol., 2016; 41:9-17. doi: 10.1016/j.coi.2016.04.005.

Borghaei et al., "Nivolumab versus Docetaxel in Advanced Nonsquamous Non-Small-Cell Lung Cancer," N Engl J Med., 2015; 373: 1627-1639.

Brahmer et al., "Nivolumab versus Docetaxel in Advanced Squamous-Cell Non-Small-Cell Lung Cancer," N Engl J Med., 2015; 373: 123-135.

Chen et al., "Quantification of β-Catenin Signaling Components in Colon Cancer Cell Lines, Tissue Sections, and Microdissected Tumor Cells using Reaction Monitoring Mass Spectrometry," J. Proteome Res., 2010; 9:4215-4227.

Chen et al., (2009) Glycoproteomics analysis of human liver tissue by combination of multiple enzyme digestion and hydrazide chemistry. J Proteome Res 8, 651-661.

Chen et al., (2016) Analysis of Immune Signatures in Longitudinal Tumor Samples Yields Insight into Biomarkers of Response and Mechanisms of Resistance to Immune Checkpoint Blockade. Cancer Discov 6, 827-837

Dahan et al., (2016) Therapeutic Activity of Agonistic, Human Anti-CD40 Monoclonal Antibodies Requires Selective FcgammaR Engagement. Cancer Cell 29, 820-831.

(Continued)

*Primary Examiner* — Jerry Lin
(74) *Attorney, Agent, or Firm* — Michael Best & Friedrich LLP

(57) ABSTRACT

The present disclosure relates generally to the analysis of immune checkpoint proteins involved in cancer. In particular, the present disclosure provides material and methods for determining abundance ratios of various immune checkpoint proteins (e.g., PD-1, PD-L1, and PD-L2) present in a biospecimen sample based on quantification of peak area using mass spectrometry analysis. The methods disclosed herein provide an alternative platform for diagnosing and treating cancer, especially in cases limited by ineffective antibody recognition.

10 Claims, 17 Drawing Sheets

Specification includes a Sequence Listing.

(56) References Cited

OTHER PUBLICATIONS

Danilova et al., (2016) Association of PD-1/PD-L axis expression with cytolytic activity, mutational load, and prognosis in melanoma and other solid tumors. Proc Natl Acad Sci U S A 113, E7769-E7777.
Daud et al., (2016) Programmed Death-Ligand 1 Expression and Response to the Anti-Programmed Death 1 Antibody Pembrolizumab in Melanoma. J Clin Oncol 34, 4102-4109.
Dezutter-Dambuyant et al., (2016) A novel regulation of PD-1 ligands on mesenchymal stromal cells through MMP-mediated proteolytic cleavage. Oncoimmunology 5, e1091146, 24 pages.
Drabovich et al., (2012) Quantitative analysis of energy metabolic pathways in MCF-7 breast cancer cells by selected reaction monitoring assay. Mol Cell Proteomics 11, 422-434.
Federspiel et al., (2016) Assembly Dynamics and Stoichiometry of the Apoptosis Signal-regulating Kinase (ASK) Signalosome in Response to Electrophile Stress. Mol Cell Proteomics 15, 1947-1961.
Ferris et al., (2016) Nivolumab for Recurrent Squamous-Cell Carcinoma of the Head and Neck. N Engl J Med, 12 pages.
Gallien et al., "Targeted proteomic quantification on quadrupole-orbitrap mass spectrometer," Mol Cell Proteomics. Dec. 2012;11(12):1709-23.
Gold et al., "Aptamer-based multiplexed proteomic technology for biomarker discovery," PLoS One. Dec. 7, 2010;5(12):e1500, 17 pages.
Hutton et al., (2016) Oncogenic KRAS and BRAF Drive Metabolic Reprogramming in Colorectal Cancer. Mol Cell Proteomics 15, 2924-2938.
International Search Report and Written Opinion for Application No. PCT/US2016/028426, dated Jul. 18, 2016, 9 pages.
Joyce et al., (2015) T cell exclusion, immune privilege, and the tumor microenvironment. Science 348, 74-80.
Keir et al., PD-1 and its ligands in tolerance and immunity, Annu Rev Immunol, 2008; 26, 677-704.
Kikuchi et al., "In-depth proteomic analysis of nonsmall cell lung cancer to discover molecular targets and candidate biomarkers," Mol Cell Proteomics. Oct. 2012;11(10):916-32.
Kim et al., (2016) Quantitative Profiling of Protein Tyrosine Kinases in Human Cancer Cell Lines by Multiplexed Parallel Reaction Monitoring Assays. Mol Cell Proteomics 15, 682-691.
Larkin et al., "Combined Nivolumab and Ipilimumab or Monotherapy in Untreated Melanoma," N Engl J Med., 2015; 373, 23-34.
Latchman et al., (2001) PD-L2 is a second ligand for PD-1 and inhibits T cell activation. Nat Immunol 2, 261-268.
Le Mercier et al., (2014) VISTA Regulates the Development of Protective Antitumor Immunity. Cancer Res 74, 1933-1944.
Lee et al., (2014) Abundance-ratio-based semiquantitative analysis of site-specific N-linked glycopeptides present in the plasma of hepatocellular carcinoma patients. J Proteome Res 13, 2328-2338.
Li et al., (2016) Glycosylation and stabilization of programmed death ligand-1 suppresses T-cell activity. Nat Commun 7, 12632, 11 pages.
Lines et al., (2014) VISTA is a novel broad-spectrum negative checkpoint regulator for cancer immunotherapy. Cancer Immunol Res 2, 510-517.
Lizotte et al., (2016) Multiparametric profiling of non-small-cell lung cancers reveals distinct immunophenotypes. JCI Insight 1, e89014, 18 pages.
Maclean et al., "Skyline: an open source document editor for creating and analyzing targeted proteomics experiments," Bioinformatics. Apr. 1, 2010;26(7):966-8.
Mahoney et al., (2015) Combination cancer immunotherapy and new immunomodulatory targets. Nat Rev Drug Discov 14, 561-584
Mani et al., "Statistical characterization of multiple-reaction monitoring mass spectrometry (MRM-MS) assays for quantitative proteomics," BMC Bioinformatics. 2012; 13 Suppl 16:S9, 18 pages.
Motzer et al., "Nivolumab versus Everolimus in Advanced Renal-Cell Carcinoma," N Engl J Med., 2015; 373, 1803-1813.
Nguyen et al., (2015) Clinical blockade of PD1 and LAG3—potential mechanisms of action. Nat Rev Immunol 15, 45-56.
Pardoll, "The blockade of immune checkpoints in cancer immunotherapy," Nat Rev Cancer, 2012; 12, 252-264.
Peterson et al., (2012) Parallel reaction monitoring for high resolution and high mass accuracy quantitative, targeted proteomics. Mol Cell Proteomics 11, 1475-1488.
Platten et al., (2014) Cancer Immunotherapy by Targeting IDO1/TDO and Their Downstream Effectors. Front Immunol 5, 673, 7 pages.
Polyakova et al., "Proteogenomics meets cancer immunology: mass spectrometric discovery and analysis of neoantigens," Expert Rev. Proteomics,2015; 12(5): 533-541.
Rauniyar, "Parallel Reaction Monitoring: A Targeted Experiment Performed Using High Resolution and High Mass Accuracy Mass Spectrometry," Int J Mol Sci. Dec. 2015; 16(12):28566-28581.
Reck et al., (2016) Pembrolizumab versus Chemotherapy for PD-L1-Positive Non-Small-Cell Lung Cancer. N Engl J Med. 1823-1833.
Ribas et al., "Pembrolizumab versus investigator-choice chemotherapy for ipilimumab-refractory melanoma (KEYNOTE-002): a randomised, controlled, phase 2 trial," Lancet Oncol, 2015; 16, 908-918.
Rizvi et al., (2015) Cancer immunology. Mutational landscape determines sensitivity to PD-1 blockade in non-small cell lung cancer. Science 348, 124-128.
Robert et al., "Pembrolizumab versus Ipilimumab in Advanced Melanoma," N Engl J Med., 2015; 372, 2521-2532.
Rosenberg et al., (2016) Atezolizumab in patients with locally advanced and metastatic urothelial carcinoma who have progressed following treatment with platinum-based chemotherapy: a single-arm, multicentre, phase 2 trial. Lancet 387, 1909-1920.
Rosner et al., (1982) Separation of glycopeptides by high performance liquid chromatography. J Cell Biochem 18, 37-47.
Schumacher et al., (2015) Neoantigens in cancer immunotherapy. Science 348, 69-74.
Sharma et al., (2015) Immune checkpoint targeting in cancer therapy: toward combination strategies with curative potential. Cell 161, 205-214
Sharma et al., (2016) Nivolumab monotherapy in recurrent metastatic urothelial carcinoma (CheckMate 032): a multicentre, open-label, two-stage, multi-arm, phase 1/2 trial. Lancet Oncol 17, 1590-1598.
Shi et al., (2012) Antibody-free, targeted mass-spectrometric approach for quantification of proteins at low picogram per milliliter levels in human plasma/serum. Proc Natl Acad Sci U S A 109, 15395-15400.
Sholl et al., (2016) Programmed Death Ligand-1 Immunohistochemistry—A New Challenge for Pathologists: A Perspective From Members of the Pulmonary Pathology Society. Arch Pathol Lab Med 140, 341-344.
Sjöström et al., "A Combined Shotgun and Targeted Mass Spectrometry Strategy for Breast Cancer Biomarker Discovery," J Proteome Res. Jul. 2, 2015;14(7):2807-18. doi: 10.1021/acs.jproteome. 5b00315. Epub Jun. 5, 2015.
Sprung et al., (2012) Precision of multiple reaction monitoring mass spectrometry analysis of formalin-fixed, paraffin-embedded tissue. J Proteome Res 11, 3498-3505.
Sunshine et al., (2015) PD-1/PD-L1 inhibitors. Curr Opin Pharmacol 23, 32-38.
Topalian et al., "Mechanism-driven biomarkers to guide immune checkpoint blockade in cancer therapy," Nature Reviews Cancer 16, 275-287 (2016).
Tumeh et al., "PD-1 blockade induces responses by inhibiting adaptive immune resistance," Nature. Nov. 27, 2014;515(7528):568-71.
Yoshihara et al., "Inferring tumour purity and stromal and immune cell admixture from expression data," Nat Commun. 2013; 4:2612, 11 pages.
Youngnak et al., (2003) Differential binding properties of B7-H1 and B7-DC to programmed death-1. Biochem Biophys Res Commun 307, 672-677.

(56) References Cited

OTHER PUBLICATIONS

Zak et al., (2015) Structure of the Complex of Human Programmed Death 1, PD-1, and Its Ligand PD-L1. Structure 23, 2341-2348.
Zhang et al., "Proteogenomic characterization of human colon and rectal cancer," Nature. Sep. 18, 2014;513(7518):382-7.
Zhang et al., (2011) Methods for peptide and protein quantitation by liquid chromatography-multiple reaction monitoring mass spectrometry. Mol Cell Proteomics 10, M110 006593.
Zou et al., (2016) PD-L1 (B7-H1) and PD-1 pathway blockade for cancer therapy: Mechanisms, response biomarkers, and combinations. Sci Transl Med 8, 328rv324.
European Patent Office Examination Report for Application No. 16862613.3 dated Mar. 25, 2020 (4 pages).
Translation of Japanese Patent Office Action for Application No. 2018-542117 dated Apr. 7, 2020 (2 pages).
European Patent Office Search Report for Application No. 16862613.3 dated Apr. 1, 2019, 7 pages.

INTTTNEIFYCTFR

IDTTTNEIFYCTFR (fragments with m/z shift from N → D substitution labeled in red)

IMMUNE CHECKPOINT MOLECULAR FITNESS PROFILING BY MASS SPECTROMETRY

RELATED APPLICATIONS

This application claims priority to and the benefit of U.S. Provisional Application Ser. No. 62/461,092 filed on Feb. 20, 2017. This application is incorporated herein by reference in its entirety for all purposes.

STATEMENT REGARDING FEDERALLY SPONSORED RESEARCH

This invention was made with U.S. Government support under grant numbers U24CA159988 and K23CA204726 awarded by the National Institutes of Health. The U.S. Government has certain rights in this invention.

SEQUENCE LISTING

The sequence listing is filed with the application in electronic format only and is incorporated by reference herein. The sequence listing text file "093386-9176-US02_As_Filed_Sequence_Listing.txt" was created on Feb. 20, 2018, and is 3,268 bytes in size.

TECHNICAL FIELD

The present disclosure relates generally to the analysis of immune checkpoint proteins involved in cancer. In particular, the present disclosure provides material and methods for determining abundance ratios of various immune checkpoint proteins (e.g., PD-1, PD-L1, and PD-L2) present in a biospecimen sample based on quantification of peak area using combined mass spectrometry analysis. The methods disclosed herein provide an alternative platform for diagnosing and treating cancer, especially in cases limited by ineffective antibody recognition.

BACKGROUND

Various disorders and diseases, including cancers, arise from alterations in the sequence, structure, or expression of genes that control cell function, growth, and differentiation. These alterations lead to distinct sets of changes in RNAs, proteins and other biomolecules, which drive clinically important characteristics, such as the propensity of a cancer to invade nearby tissues, metastasize to other organs and respond to therapies. Of these molecular features, proteins are often the targets of drugs for disease treatment. In some cases, drugs are targeted specifically to protein sequence variants encoded by genes that are mutated or dysregulated in cancers or other diseases. Diagnostic tests may also measure other proteins that are not themselves targets, but which affect the functions of drug targets and thereby influence the response of a disease to treatment.

The predominant method to analyze proteins in tissue specimens is immunohistochemistry (IHC), in which a protein of interest is detected in a thin tissue section by reaction with an antibody, followed by a staining procedure that enables visualization of the antibody-detected proteins by microscopy. Because a skilled pathologist can distinguish different cell types and stroma in the section, the association of the staining with the cells of interest or surrounding stroma can be verified, thereby providing evidence of association of the detected protein with the cells of interest, such as cancer cells.

Despite widespread use, IHC has significant limitations. IHC analysis requires an antibody that specifically and selectively binds to the protein of interest in a section. For many proteins, antibodies with the necessary performance characteristics for IHC cannot be obtained. In the most widely used diagnostic implementation, IHC detects one protein in each of one or more thin sections of a tissue specimen tested, and the measurement of multiple protein features is practically limited. Moreover, many IHC tests fail to yield interpretable results because of problems with the antibody recognition of the target protein or with the staining chemistry and because of variability in quality of the tissue sections due to sample handling, processing, and storage.

SUMMARY

Embodiments of the present disclosure include a method of calculating an abundance ratio from a biospecimen using combined mass spectrometry analysis. In accordance with these embodiments, the method includes quantifying peak area of two peptide fragments isolated from a biospecimen corresponding to at least two of programmed cell death 1 (PD-1), programmed cell death 1 ligand 1 (PD-L1), and programmed cell death 1 ligand 2 (PD-L2) using combined mass spectrometry analysis; and calculating an abundance ratio based on the quantified peak area of the two peptide fragments corresponding to the at least two PD-1, PD-L1, and PD-L2.

Embodiments of the present disclosure also include a method of treating cancer in a subject in need thereof. In accordance with these embodiments, the method includes quantifying peak area of two peptide fragments isolated from a biospecimen from the subject corresponding to at least two of programmed cell death 1 (PD-1), programmed cell death 1 ligand 1 (PD-L1), and programmed cell death 1 ligand 2 (PD-L2) using combined mass spectrometry analysis; calculating an abundance ratio based on the quantified peak area of the two peptide fragments corresponding to the at least two PD-1, PD-L1, and PD-L2; and administering an anticancer therapeutic to the subject based on the calculated abundance ratio.

The present disclosure provides a method for quantifying one or more immune checkpoint proteins in a sample in a combined mass spectrometry analysis. The one or more immune checkpoint proteins may be PD-1, PD-L1, or PD-L2. The immune checkpoint proteins may be post-translationally modified, such as by glycosylation. The methods disclosed treating cancer in a subject, including quantifying one or more immune checkpoint proteins and selecting an anticancer treatment based upon levels of the one or more immune checkpoint proteins in the sample.

In some embodiments, the present disclosure provides methods of quantifying PD-1 and PD-L1 in a sample. Such methods may comprise obtaining a biospecimen from a human subject and quantifying levels of PD-1 and PD-L1 in the biospecimen in a combined mass spectrometry analysis.

In some embodiments, the present disclosure provides methods of quantifying PD-1 and PD-L2 in a sample, including obtaining a biospecimen from a human subject and quantifying the levels of PD-1 and PD-L2 in the biospecimen in a combined mass spectrometry analysis.

In some embodiments, the present disclosure provides methods of quantifying levels of functionally active immune checkpoint proteins in a sample, including obtaining a biospecimen from a human subject; quantifying functionally active PD-L1 in the biospecimen by mass spectrometry targeting a PD-L1 binding site peptide; and quantifying PD-L1 in the biospecimen by mass spectrometry targeting a PD-L1 core peptide.

In some embodiments, the present disclosure provides methods of quantifying levels of functionally active immune checkpoint proteins in a sample. Such methods include obtaining a biospecimen from a human subject; quantifying functionally active PD-L2 in the biospecimen by mass spectrometry targeting a PD-L2 binding site peptide; and quantifying PD-L2 in the biospecimen by mass spectrometry targeting a PD-L2 core peptide.

In some embodiments, the present disclosure provides methods of treating cancer in a subject in need thereof. The methods include obtaining a biospecimen from the subject; quantifying levels of functionally active PD-L1 in the biospecimen by mass spectrometry targeting a PD-L1 binding site peptide; quantifying levels of PD-L1 in the biospecimen by mass spectrometry targeting a PD-L1 core peptide; and administering an anti-PD-L1 therapeutic to the subject if levels of functionally active PD-L1 in the biospecimen are substantially equivalent to levels of PD-L1 in the biospecimen.

In some embodiments, the present disclosure provides methods of treating cancer in a subject in need thereof, including obtaining a biospecimen from the subject; quantifying levels of functionally active PD-L2 in the biospecimen by mass spectrometry targeting a PD-L2 binding site peptide; quantifying levels of PD-L2 in the biospecimen by mass spectrometry targeting a PD-L2 core peptide; and administering an anti-PD-L2 therapeutic to the subject if levels of functionally active PD-L2 in the biospecimen are substantially equivalent to levels of PD-L2 in the biospecimen.

In some embodiments, the present disclosure provides methods for treating cancer in a subject in need thereof, including obtaining a biospecimen from the subject; quantifying levels of PD-1 and PD-L1 in the biospecimen by mass spectrometry; selecting an anticancer treatment based upon the levels of PD-1 and PD-L1 in the biospecimen; and administering the anticancer treatment to the subject.

In some embodiments, the present disclosure provides methods for treating cancer in a subject including obtaining a biospecimen from the subject; quantifying levels of PD-1 and PD-L2 in the biospecimen by mass spectrometry; selecting an anticancer treatment based upon levels of PD-1 and PD-L2 in the biospecimen; and administering the anticancer treatment to the subject.

In some embodiments, the present disclosure provides methods for treating cancer in a subject, including obtaining a biospecimen from the subject; determining levels of PD-1, PD-L1, and PD-L2 in the biospecimen by mass spectrometry; selecting an anticancer treatment based upon levels of PD-1, PD-L1, and PD-L2 in the biospecimen; and administering the anticancer treatment to the subject.

In some embodiments, the present disclosure provides methods of screening a human subject for treatment with an anticancer agent, including obtaining a biospecimen from the subject; quantifying a level of PD-1 in the biospecimen by mass spectrometry; and quantifying a level of PD-L1 in the biospecimen by mass spectrometry. The quantified levels of PD-1 and PD-L1 may indicate responsiveness to an anti-PD-1 therapeutic if the quantified level of PD-L1 exceeds the quantified level of PD-1. The quantified levels of PD-1 and PD-L1 may indicate responsiveness to an anti-PD-L1 therapeutic if the quantified level of PD-1 exceeds the quantified level of PD-L1.

In some embodiments, the present disclosure provides methods of screening a human subject for treatment with an anticancer agent, including obtaining a biospecimen from the subject; quantifying a level of PD-1 in the biospecimen by mass spectrometry; and quantifying a level of PD-L2 in the biospecimen by mass spectrometry. The quantified levels of PD-1 and PD-L2 may indicate responsiveness to an anti-PD-1 therapeutic if the quantified level of PD-L2 exceeds the quantified level of PD-1, and the quantified levels of PD-1 and PD-L2 may indicate responsiveness to an anti-PD-L1 therapeutic if the quantified level of PD-1 exceeds the quantified level of PD-L2.

In some embodiments, the present disclosure provides methods for treating cancer in a subject in need thereof. Such disclosed methods may comprise obtaining a biospecimen from the subject; quantifying a level of PD-1 in the biospecimen by mass spectrometry; quantifying a level of PD-L1 in the biospecimen by mass spectrometry; and administering an anti-PD-1 therapeutic antibody to the subject if the quantified level of PD-L1 exceeds the quantified level of PD-1.

In some embodiments, the present disclosure provides methods for treating cancer in a subject in need thereof, including obtaining a biospecimen from the subject; quantifying a level of PD-1 in the biospecimen by mass spectrometry; quantifying a level of PD-L2 in the biospecimen by mass spectrometry; and administering an anti-PD-1 therapeutic antibody to the subject if the quantified level of PD-L2 exceeds the quantified level of PD-1.

In some embodiments, the present disclosure provides methods for treating cancer in a subject in need thereof. Such methods can include obtaining a biospecimen from the subject; quantifying a level of PD-1 in the biospecimen by mass spectrometry; quantifying a level of PD-L1 in the biospecimen by mass spectrometry; and administering an anti-PD-L1 therapeutic antibody to the subject if the quantified level of PD-1 exceeds the quantified level of PD-L1.

In some embodiments, the present disclosure provides methods for treating cancer in a subject in need thereof, including obtaining a biospecimen from the subject; quantifying a level of PD-1 in the biospecimen by mass spectrometry; quantifying a level of PD-L2 in the biospecimen by mass spectrometry; and administering an anti-PD-L2 therapeutic antibody to the subject if the quantified level of PD-1 exceeds the quantified level of PD-L2.

In some embodiments, the present disclosure provides methods of quantifying levels of post-translationally modified immune checkpoint proteins in a sample. In accordance with these embodiments, the method includes obtaining a biospecimen from a human subject; quantifying post-translationally modified PD-L1 in the biospecimen by mass spectrometry targeting a post-translationally modified PD-L1 peptide; and quantifying PD-L1 in the biospecimen by mass spectrometry targeting a PD-L1 core peptide.

In some embodiments, the present disclosure provides methods for treating cancer in a subject in need thereof, including obtaining a biospecimen from a human subject; quantifying post-translationally modified PD-L1 in the biospecimen by mass spectrometry targeting a post-translationally modified PD-L1 peptide; quantifying total PD-L1 in the biospecimen by mass spectrometry targeting a PD-L1 core peptide; selecting an anticancer treatment based upon the levels of post-translationally modified PD-L1 and total PD-L1 in the biospecimen; and administering the anticancer treatment to the subject.

In some embodiments, the present disclosure provides methods for treating cancer in a subject in need thereof, including obtaining a biospecimen from a human subject; quantifying post-translationally modified PD-L1 in the biospecimen by mass spectrometry targeting a post-translationally modified PD-L1 peptide; quantifying total PD-L1 in the biospecimen by mass spectrometry targeting a PD-L1 core peptide; and administering an anti-PD-1 therapeutic antibody if the quantified post-translationally modified PD-L1 in the biospecimen substantially equals the quantified total PD-L1 in the biospecimen.

In some embodiments, the present disclosure provides methods for treating cancer in a subject in need thereof. In accordance with these embodiments, the method includes obtaining a biospecimen from a human subject; quantifying post-translationally modified PD-L1 in the biospecimen by mass spectrometry targeting a post-translationally modified PD-L1 peptide; quantifying total PD-L1 in the biospecimen by mass spectrometry targeting a PD-L1 core peptide; and administering an anti-PD-L1 therapeutic antibody if the quantified total PD-L1 in the biospecimen substantially exceeds the quantified post-translationally modified PD-L1 in the biospecimen.

Additional aspects and embodiments of the disclosure will be set forth and described herein.

DETAILED DESCRIPTION

Figure 1:
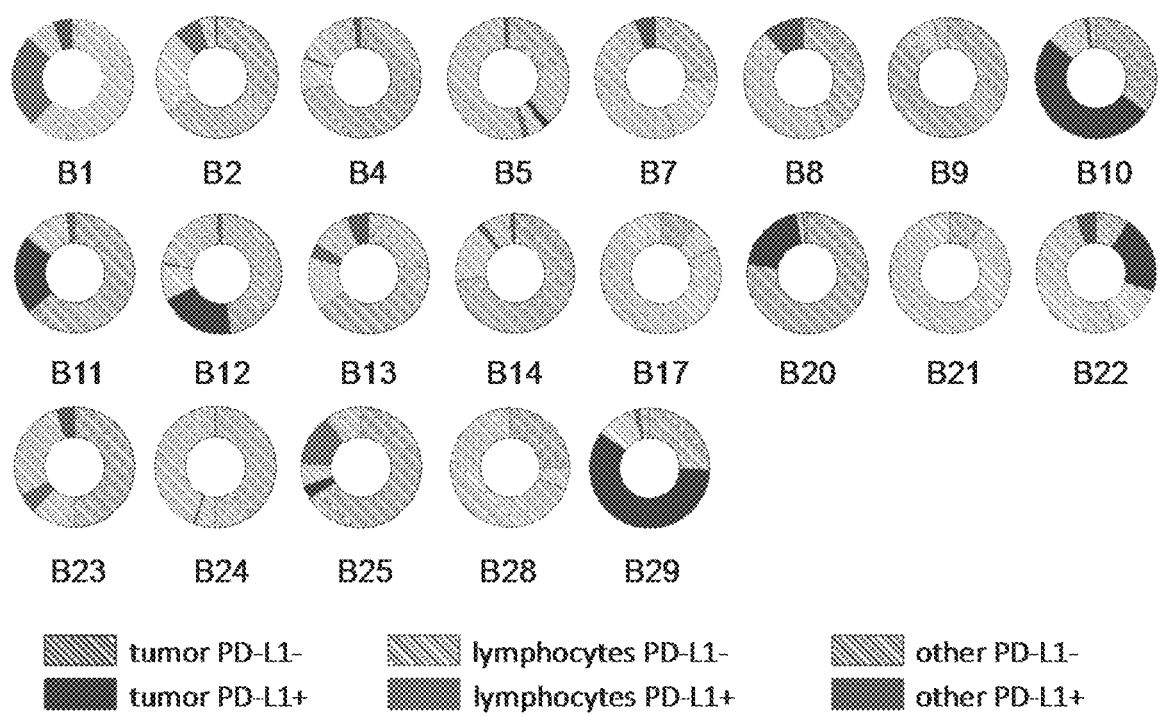
FIG. 1 shows the cellular composition and IHC PD-L1-positive fraction of cell classes in 22 melanoma samples. Donut plots indicate tumor cells (red), lymphocytes/histiocytes (dark green) and other cell types (blue). Solid color indicates PD-L1 positive cells, hashed color indicates PD-L1 negative cells.

Immune checkpoint proteins, such as programmed cell death 1 (PD-1, PDCD1) and its ligands programmed cell death 1 ligand 1 (PD-L1, CD274) and programmed cell death 1 ligand 2 (PD-L2, PDCD1LG2) mediate inhibition of CD8+ effector T-cells. In the microenvironment of many tumors, binding of T-cell PD-1 to PD-L1 and/or PD-L2 on tumor cells, lymphocytes or macrophages inactivates CD8+ T-cells, thereby protecting tumors from destruction by the immune system. Inhibition of the PD-1/PD-L1 interaction with administration of therapeutic antibodies, such as anti-PD-1 therapeutic antibodies, anti-PD-L1 therapeutic antibodies, and anti-PD-L2 therapeutic antibodies may provide effective immunotherapy for several cancers, including melanoma, renal clear cell carcinoma, non-small cell lung cancer, urothelial carcinoma, colon and rectal carcinoma, and head and neck carcinoma. Such therapeutic antibodies include, for example, pembrolizumab, nivolumab, pidilizumab, ipilimumab, avelumab, durvalumab, or atezolizumab.

One question in immuno-oncology is which patients will benefit from immune checkpoint therapeutics. Objective responses are seen in only 20-50% of patients treated with immune checkpoint drugs, which indicates both incomplete mechanistic understanding of the tumor-immune interface and a paucity of biomarkers for critical features. The principal biomarker used to predict therapeutic response to immune checkpoint therapeutics is the PD-L1 protein, which is currently measured by those of ordinary skill in the art using antibody-based techniques, principally immunohistochemistry (IHC). Although PD-L1 is the most extensively studied PD-1 ligand, PD-L2 also can inactivate T-cells by binding to PD-1. PD-L2 binds to PD-1 with approximately 2-6 fold higher affinity than does PD-1, as estimated by flow cytometry and surface plasmon resonance. However, interest in PD-L2 had been tempered by the apparently low expression of the protein in solid tumors, although low PD-L2 expression may reflect the relatively poor performance of available PD-L2 antibodies for IHC. A recently developed PD-L2 antibody suitable for IHC detected PD-L2 protein in multiple cancer specimens. Conventional, antibody-based measurements of PD-1, PD-L1, and PD-L2 also may be affected by glycosylation, which may directly inhibit antibody binding or alter protein structure, thereby affecting antibody binding sites.

A PD-L1 IHC test is approved as a companion diagnostic for pembrolizumab. Other PD-L1 IHC tests are approved as complementary diagnostics for nivolumab, atezolizumab, durvalumab and avelumab. PD-L1 IHC tests are approved as companion diagnostics for pembrolizumab and atezolizumab. However, conventional measurement of PD-L1 expression by IHC is an unreliable predictor of individual therapeutic responses. Across several reported clinical trials, up to half of PD-L1 IHC-positive tumors failed to respond to therapy, whereas approximately 15% of PD-L1 IHC-negative tumors did respond. Clinical application of PD-L1 IHC is further complicated by the availability of four commercially available tests, which employ different antibodies and different cutoffs for assessment. Several other factors also influence responses to immune checkpoint therapeutics, including tumor neoantigen load and expression, extent of T-cell infiltration and composition of T-cell subsets, and activities of other immune checkpoint proteins, co-stimulators, and inhibitory molecules.

Analysis by mass spectrometry (MS) provides a powerful new alternative to IHC for the measurement of proteins in tissues. For MS analyses, a tissue specimen may be homogenized and subjected to protein extraction, and the extracted proteins may be cleaved using enzymatic or chemical reagents to form peptides, which may then be analyzed by tandem mass spectrometry techniques known as selected reaction monitoring (SRM), multiple reaction monitoring (MRM) or PRM, depending on the specific type of MS instrument used. Peptides are selectively detected by monitoring sequence-specific fragmentations. Targeted measurement of proteotypic peptide sequences specific to proteins provides a universal means to systematically configure sensitive, specific assays. Moreover, a single SRM/MRM/PRM analysis can monitor up to approximately 100 proteins in a combined assay. MS-based protein assays offer the potential to systematically implement diagnostic tests with a specificity, sensitivity, and information content that far exceeds the capacity of IHC.

Targeted MS by PRM allows sensitive, highly specific and robust quantitative analysis of proteins. PRM analysis with stable isotope-labeled internal standards (stable isotope dilution, SID) yields molar quantitation, which enables direct comparison of protein stoichiometries in functional cellular systems. Moreover, targeted MS is ideal for the analysis of clinical specimens, including FFPE sections.

The present disclosure provides methods of performing precise, accurate measurements of proteins in heterogeneous multicellular biospecimens. The present disclosure includes an addressable fractionation-PRM platform, which provides measurements of PD-1, PD-L1, and PD-L2 at femtomole per microgram tissue protein levels in a biospecimen, such as, for example, a FFPE section of a human cancer biopsy. The disclosure further compares analysis by fractionation-PRM to IHC measurements of PD-L1 in adjacent sections to further characterize the effects of variable cellular composition on measured PD-1, PD-L1 and PD-L2. The data provided herein demonstrate substantial between-tumor variation in expression ratios of these proteins and suggest that PD-L2 is present in some tumors at levels sufficient to contribute to PD-1-dependent T-cell regulation and affect responses to PD-1- and PD-L1-blocking drugs. Further provided in the present disclosure is the identification and quantitation of several N-glycosylated forms of PD-L1, providing evidence that posttranslational modifications of PD-L1 may affect PD-L1 detection by IHC. Further, the fractionation-PRM platform can be extended to the analysis of several other immune checkpoint and co-regulator proteins, which can be targets for new drug development or which affect responses to immunotherapeutics. The present disclosure provides a next-generation analysis platform to advance cancer immuno-therapeutic research and diagnostics.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are hereby incorporated by reference in their entirety. The materials, methods, and examples disclosed herein are illustrative only and not intended to be limiting.

"About" is used synonymously herein with the term "approximately." Illustratively, the use of the term "about" indicates that values slightly outside the cited values, namely, plus or minus 10%. Such values are thus encompassed by the scope of the claims reciting the terms "about" and "approximately."

"Administer," "administering," "administered," or "administration," as used herein, refer to any manner of providing a drug compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Anticancer agent(s)," as used herein, refers to any agent or combination of agents capable of affecting the development, metastasis, and/or progression of a cancer, including but not limited to, antibodies, aptamers, small molecules, and the like, and any derivatives thereof. In some embodiments, anticancer agents can include an agent or combinations of agents that interfere with immune checkpoint blockade, such as monoclonal antibodies or small molecules that inhibit or reduce interaction between PD-1 and PD-L1 or PD-L2.

"Biospecimen," as used herein, refers to a biological sample comprising cells. A biospecimen may be obtained from a subject. A biospecimen may comprise, for example, cultured cells; a tissue sample; a biopsy; a needle biopsy; a tumor sample; a biofluid such as blood; xenograft tissue such as tumor xenograft tissue; exfoliated cells such as buccal mucosa, urinary tract epithelium, airway epithelium, or gastrointestinal tract epithelium; or any other biological sample of interest. Biospecimens may be obtained through methods familiar to those of ordinary skill in the art.

"Binding site peptide," as used herein, refers to a peptide mapping to the active binding site of a functional protein. For example, a binding site peptide for PD-1 may map to the site of PD-1 that binds to PD-L1. As another example, the binding site peptide for PD-1 may map to the site of PD-1 that binds to PD-L2.

"Combined mass spectrometry," as used herein, refers to methods that include the detection and/or quantification of at least two different proteins, polypeptides, or peptide fragments using mass spectrometry analysis performed with a single run on a single sample. For example, as disclosed herein, the method can include quantifying any two different peptide fragments corresponding to PD-1, PD-L1 and/or PD-L2 in a single mass spectrometry analysis of a biospecimen sample.

"Comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

"Contacting" as used herein, e.g., as in "contacting a sample" refers to contacting a sample directly or indirectly in vitro, ex vivo, or in vivo (i.e., within a subject as defined herein). Contacting a sample may include addition of a compound to a sample (e.g., a sample of proteins extracted from a biospecimen), or administration to a subject. Contacting encompasses administration to a solution, cell, tissue, mammal, subject, patient, or human. Further, contacting a cell includes adding an agent to a cell culture.

"Core peptide," as used herein, refers to a peptide mapping to a core region of the protein of interest. A core region is not affected by post translational modifications or cleavage, and does not overlap with the binding site of the protein that mediates functional protein interactions.

"Effective amount," as used herein, refers to a dosage or an amount of a compound or a composition effective for eliciting a desired effect. This term as used herein may also refer to an amount effective at bringing about a desired in vivo effect in an animal (e.g., a mammal, such as a human). For example, in methods of treating cancer, an effective amount may be an amount sufficient to treat the disorder.

"Proteotypic," as used herein, refers to peptide sequences that are uniquely present in the protein from which they are derived in that organism and thus represent evidence that measurements of the proteotypic peptide represent only the parent protein and not other proteins present in that organism.

"Subject," as used herein, refers to human and non-human animals. Exemplary human subjects include a human patient having a disorder, e.g., cancer, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

"Target protein," as used herein, refers to a protein of interest to be measured in a heterogeneous biospecimen. The amount of a target protein expressed by at least one cell type in a biospecimen may vary between heterogeneous biospecimens obtained from different subjects or from the same subject at different times or different anatomical locations. In some embodiments, a target protein may be the target of a drug or other therapies or a protein that modifies drug responses. In some embodiments, a target protein may be a protein identified or hypothesized to serve as a biomarker to predict or detect responses to therapy, to predict or detect risk of metastasis or other biological properties, or to assess disease prognosis or other clinical outcomes.

"Treat" or "treating" or "treatment" directed to a subject having a disorder, as used herein, refers to administering a compound or a composition described herein to the subject, such that at least one symptom of the disorder is cured, healed, alleviated, relieved, altered, remedied, ameliorated, or improved. Treating includes administering an amount of a compound or a composition to effective to alleviate, relieve, alter, remedy, ameliorate, cure, improve or affect the disorder or the symptoms of the disorder. The treatment may inhibit deterioration or worsening of a symptom of a disorder.

2. Methods for Quantifying Immune Checkpoint Proteins

In some embodiments, the disclosed methods can be used to quantify one or more immune checkpoint proteins in a biospecimen. Exemplary checkpoint proteins include, but are not limited to, PD-1, PD-L1, and PD-L2. Other checkpoint proteins which may be measured using the disclosed methods include IDO1, TDO2, LAG3, HAVCR2 (TIM-3), VISR (VISTA, C10orf54), TNFRSF9 (4-1BB), CD40, CD40L, CD27, OX40, OX40L, GITR, TIGIT, STING, CD122, CD137, CD28, ICOS, ICOSLG, A2AR, CD276 (B7-H3), VTCN1 (B7-H4), TNFRSF17 (BCMA), BTLA, CTLA-4, NT5E (CD73), CEACAM1 and KIR.

Methods provided herein may be used to quantify any combination of one or more checkpoint proteins in a biospecimen. In some embodiments, the methods include means for quantifying one or more immune checkpoint proteins in a biospecimen, wherein the immune checkpoint proteins are selected from the group consisting of PD-1, PD-L1, and PD-L2. For example, the disclosed methods may be used to quantify PD-1, PD-L1, PD-L2, PD-1 and PD-L1, PD-1 and PD-L2, and/or PD-L1 and PD-L2. The disclosed methods may also be used to quantify PD-1, PD-L1, and PD-L2. The above recitations are provided solely for the purpose of exemplifying possible combinations of proteins and are not intended to limit the scope of the invention in any way. In addition, one or more immune checkpoint proteins may be quantified separately in parallel MS analysis or together in a single combined MS analysis.

A biospecimen of interest may be obtained from any desired source using methods and techniques familiar to those of ordinary skill in the art. Proteins may be extracted from a biospecimen using techniques known to those of ordinary skill in the art, such as by acid precipitation, organic solvent precipitation, extraction with detergents or aqueous and organic solvent mixtures, among others. Extraction may employ methods of cell and tissue disruption, including sonication, cryopulverization, mechanical disruption with beads, and extrusion through membranes. Proteins may be extracted using techniques that yield total protein samples representative of all proteins present in the biospecimen, or in some embodiments, extraction techniques may be used that result in more selective representation of proteins in the biospecimen, such as fractionation techniques that include, for example, selection or enrichment of proteins within a desired molecular weight range or isoelectric point range or based on physical characteristics, such as hydrophobicity. In some embodiments, proteins may be captured through affinity binding to one or more other molecules, such as a protein, an antibody, a small molecule probe, a lectin, or a nucleic acid aptamer. In some embodiments, proteins may be analyzed in a biospecimen without performing an extraction procedure, such as, for example, when the biospecimen comprises a biofluid.

In some embodiments, proteins may be cleaved to form peptides by any suitable approach known in the art. For example, proteins may be cleaved by contacting the proteins with a proteolytic enzyme, such as, for example, one or more of trypsin, chymotrypsin, endoproteinase Asp-N, endoproteinase Lys-C, endoproteinase Glu-C, and subtilisin. In some embodiments, the proteins may be cleaved using a chemical reagent, such as, for example, cyanogen bromide.

A target protein for MS analysis may be, for example, a target of a drug or other therapy, a protein that modifies a drug response, or a protein identified or hypothesized to serve as a biomarker to predict or detect a response to a therapy, a risk of metastasis or other biological property, or to assess a disease prognosis or other clinical outcome. Diseases of interest may include neoplasms, tumors, or cancers, such as carcinomas; immune-mediated diseases such as rheumatoid arthritis; immune inflammatory disorders; metabolic diseases; or any other disease or disorder of interest. A target protein may be selected from public or proprietary data or prior knowledge or hypotheses regarding its role as a target of a therapeutic or as a modulator of response to a therapeutic or as a contributor to a phenotypic characteristic of a disease, tumor, or metastasis. A target protein may be selected by analysis of DNA, RNA, or protein from a biospecimen associated with a disease of interest, such as a cancer, or from a cellular or xenograft model of a disease. A target protein also may be selected by computational analysis or modeling of a biological system, including a biological network, interactome, pathway, or cellular or extracellular system component, such as an organelle or extracellular matrix. In some embodiments, a target protein may be a sequence variants resulting from single nucleotide DNA sequence polymorphisms, somatic DNA mutations, insertions, deletions or chromosomal rearrangements. In some embodiments, a target protein may be a sequence variant generated during RNA processing.

In some embodiments, cleaved peptides may be analyzed by liquid chromatography-tandem mass spectrometry. For example, peptides may be analyzed without initial fractionation or may initially be fractionated by ion exchange chromatography, by high pH reverse phase chromatography, by basic reverse phase liquid chromatography, by hydrophilic interaction chromatography, by isoelectric focusing, by antibody capture or immunoprecipitation or by other fractionation techniques known to those of ordinary skill in the art. The peptide fractions or mixtures then may be analyzed by reverse phase liquid chromatography coupled to electrospray tandem mass spectrometry. Several tandem mass spectrometry instruments are commonly used, including ion trap, Orbitrap, time of flight, triple quadrupole, hybrid quadrupole-Orbitrap, hybrid quadrupole-time of flight, ion mobility and ion cyclotron resonance mass spectrometers. These analyses record full-scan mass spectra of peptide ions, which may include high-resolution scans capable of indicating isotopic composition and charge states of the peptide ions. Fragmentation of the peptide ions by collision-induced dissociation, high energy collision-induced dissociation, electron transfer dissociation, electron capture dissociation, and infrared multiphoton dissociation produces tandem mass spectra, which represent energetic cleavages of the peptide ions along the peptide sequence. Peptide sequences encoded by the tandem mass spectra can be identified by database search algorithms and software through procedures that are familiar to those of ordinary skill in the art.

Quantitative measurements of proteotypic peptides can be made by targeted measurement of peptide ions and their fragments in tandem mass spectrometry. Such methods may include SRM, MRM, or PRM, depending on the type of tandem mass spectrometer used. With heavy isotope-labeled peptide standards and calibration curves, accurate and precise quantitation of proteotypic peptides can be achieved.

Proteotypic peptides may be selected for a target protein using criteria for proteotypic peptide selection known to those of ordinary skill in the art. For example, approaches for selecting a proteotypic peptide to be measured in a spectrometry-based assay may include, for example, the use of bioinformatics, prediction algorithms, and mining of empirical data. One advantage of selecting proteotypic peptides using empirical mass spectrometry data is that such peptides are known to be detectable, which therefore increases the success of subsequent MS-based assays. Guidelines for selecting a proteotypic peptide may include selecting a peptide that is unique to a single gene product and selecting a peptide that is observable by mass spectrometry are the most prevalently used filtering criteria. In some embodiments, criteria regarding optimal peptide length, hydrophobicity, and exclusion of reactive amino acid residues may also be used in proteotypic peptide selection.

In some embodiments, the proteotypic peptides may be selected to quantify functionally active forms of one or more immune checkpoint proteins in a biospecimen. In some embodiments, MS analysis of one or more core peptides may be used to quantify the total level of a target protein. In some embodiments, MS analysis of one or more binding site peptides may be used to quantify the level of functionally active forms of a target protein. For example, MS analysis of one or more binding site peptides for PD-1 may be used to quantify the amount of PD-1 capable of binding PD-L1. As another example, MS analysis of one or more binding site peptides for PD-1 may be used to quantify the amount of PD-1 capable of binding PD-L2. In some embodiments, the proportion of a target protein in a biospecimen that is functionally active may be quantified by normalizing the level of functionally active forms of the target protein to the total level of the target protein quantified in the biospecimen.

In some embodiments, the disclosed methods may be used to quantify post-translationally modified forms of one or more immune checkpoint proteins in a biospecimen. In some embodiments, the disclosed methods may be used to identify post-translationally modified forms of one or more immune checkpoint proteins. A post-translationally modified protein may be quantified in a biospecimen by MS analysis targeting a post-translationally modified peptide from the protein. In some embodiments, the total level the protein may be quantified by MS analysis targeting a core peptide from the protein. In some embodiments, the disclosed methods may be used to quantify the proportion of a protein in a biospecimen that is post-translationally modified by comparing the quantified level of a post-translationally modified peptide from the protein to the level of a core peptide from the protein. In some embodiments, the disclosed methods may be used to identify the site of one or more post-translational modifications within an immune checkpoint protein. Post-translational modifications may include addition of one or more functional groups, proteins, or peptides to the protein of interest. Other post-translational modifications may include chemical modifications of one or more amino acids in the protein of interest. Other post-translational modifications include post-translational cleavage of one or more peptide bonds in the protein of interest. Exemplary post-translational modifications include, but are not limited to, phosphorylation, acetylation, N-linked glycosylation, amidation, hydroxylation, methylation, O-linked glycosylation, ubiquitylation, sulfation, sumoylation, palmitoylation, and C-linked glycosylation. In a preferred embodiment, the disclosed methods may be used to quantify N-glycosylated proteins. For example, the disclosed methods may be used to quantify N-glycosylated PD-L1.

In some embodiments, proteins may be analyzed by mass spectrometry of intact proteins. Although the most widely used approach to protein identification and quantitation by mass spectrometry is analysis of peptides produced by protein cleavage, direct measurement and quantitation of intact proteins is also possible. This approach, which is termed "top down" analysis, typically employs electrospray ionization to generate protein ions in the source of a Fourier transform ion cyclotron resonance, an ion trap or an Orbitrap mass spectrometer. The protein ions then are fragmented either by electron transfer dissociation or electron capture dissociation and the peptide fragment sequences are identified by tandem mass spectrometry. The key advantage of the top down approach is the analysis of distinct modified forms of proteins by systematic fragmentation of the intact molecules. In contrast to mass spectrometry analyses of cleaved protein preparations, measurements of proteins in "top down" analyses are based on signals for the intact proteins.

3. Methods of Treating Cancer

In some embodiments, the disclosed methods may be used in a method of treating cancer in a subject. The method of treating cancer in a subject may comprise steps of obtaining a biospecimen from the subject; quantifying levels of one or more immune checkpoint proteins in the biospecimen; selecting an anticancer treatment based upon the levels of the one or more immune checkpoint proteins in the biospecimen; and administering the anticancer treatment to the subject. The levels of the one or more immune checkpoint proteins may be quantified by mass spectrometry. The levels of the one or more immune checkpoint proteins may be quantified by mass spectrometry targeting a core peptide of the one or more immune checkpoint proteins. The one or more immune checkpoint proteins may be selected from the group consisting of PD-1, PD-L1, and PD-L2.

The anticancer treatment may be selected based upon the levels of any combination of the one or more immune checkpoint proteins in the biospecimen. For example, the anticancer treatment may be selected based upon the levels of PD-1 and PD-L1, PD-1 and PD-L2, PD-L1 and PD-L2, or PD-1, PD-L1, and PD-L2. The anticancer treatment may comprise an anti-PD1 antibody. The anticancer treatment may comprise an anti-PD-L1 antibody. The anticancer treatment may comprise an anti-PD-L2 antibody. For example, the anticancer treatment may comprise administering an anti-PD-1 therapeutic antibody to the subject if the quantified level of PD-L1 exceeds the quantified level of PD-1. The anticancer treatment may comprise administering an anti-PD-1 therapeutic antibody to the subject if the quantified level of PD-L2 exceeds the quantified level of PD-1. The anticancer treatment may comprise administering an anti-PD-L1 therapeutic antibody to the subject if the quantified level of PD-1 exceeds the quantified level of PD-L1. The anticancer treatment may comprise administering an anti-PD-L2 therapeutic antibody to the subject if the quantified level of PD-1 exceeds the quantified level of PD-L2.

In some embodiments, the method of treating cancer in a subject may comprise quantifying levels of functionally active immune checkpoint protein in the biospecimen. The levels of functionally active immune checkpoint protein may be measured by mass spectrometry targeting a binding region peptide for the immune checkpoint protein. The levels of functionally active immune checkpoint protein may be quantified in addition to the total levels of the immune checkpoint protein. The levels of functionally active and total immune checkpoint protein may be measured in a combined mass spectrometry analysis. For example, the method may comprise quantifying the levels of functionally active PD-L1 and total PD-L1. The method may comprise quantifying levels of functionally active PD-L2 and total PD-L2. The anticancer treatment may be selected based upon the levels of functionally active and total immune checkpoint protein. For example, the anticancer treatment may comprise administering an anti-PD-L1 therapeutic to the subject if the level of functionally active PD-L1 in the sample is substantially equivalent to the level of total PD-L1 in the biospecimen. The anticancer treatment may comprise administering an anti-PD-L2 therapeutic to the subject if the level of functionally active PD-L2 in the sample is substantially equivalent to the level of total PD-L2 in the biospecimen.

In some embodiments, the method of treating cancer in a subject may comprise quantifying the levels of post-translationally modified immune checkpoint protein in a biospecimen. The post-translationally modified immune checkpoint protein may be glycosylated. The levels of post-translationally modified immune checkpoint protein may be measured by mass spectrometry targeting a post-translationally modified peptide for the immune checkpoint protein. The post-translationally modified peptide for the immune checkpoint protein may further be contacted with a glycosidase. The post-translationally modified protein may not be recognized by standard antibodies in the field. For example, glycosylated PD-L1 may not be recognized by an anti-PD-L1 antibody. The levels of a post-translationally modified immune checkpoint protein in a biospecimen may be measured in addition to the total levels of the immune checkpoint protein. The levels of post-translationally modified and total immune checkpoint protein may be measured in a combined mass spectrometry analysis. For example, the method of treating cancer in a subject may comprise quantifying post-translationally modified PD-L1 and total PD-L1. The method of treating cancer in a subject may comprise quantifying post-translationally modified PD-L2 and total PD-L2. The anticancer treatment may be selected based upon the levels of post-translationally modified immune checkpoint protein and total immune checkpoint protein in the biospecimen. For example, the anticancer treatment may comprise administering an anti-PD-1 therapeutic antibody if the quantified post-translationally modified PD-L1 in the biospecimen substantially equals the quantified total PD-L1 in the biospecimen. The anticancer treatment may comprise administering an anti-PD-L1 therapeutic antibody if the quantified total PD-L1 in the biospecimen substantially exceeds the quantified post-translationally modified PD-L1 in the biospecimen.

The disclosed compounds, compositions, processes, and methods will be better understood by reference to the following examples, which are intended as an illustration of and not a limitation upon the scope of the invention. Where the term comprising is used herein, it should be understood that the disclosure also contemplates alternative embodiments consisting of or consisting essentially of the recited features.

4. Examples

The disclosed compounds, compositions, processes, and methods will be better understood by reference to the following examples, which are intended as an illustration of and not a limitation upon the scope of the invention.

Example 1: Materials and Methods

Materials and Reagents—

Recombinant human PD-L1 protein (containing a C-terminal 1G1-Fc tag) and PNGase-F were purchased from Thermo Fisher Scientific (Waltham, Mass., USA) and Promega (Madison, Wis., USA), respectively. Sep-Pak C18 desalting cartridges (1 cc, 100 mg) and XBridge C18 (4.6× 250 mm, 5 µm) columns were from Waters (Milford, Mass.). ReproSil C18-AQ resin (3 µm particle size) was purchased from Dr. Maisch, Gmbh (Ammerbuch-Entringen, Germany). Picofrit self-pack columns (75 µm ID, 10 µm ID tip) were from New Objective (Woburn, Mass.). An equimolar predigested bovine 6 protein mix used as an MS system performance standard was purchased from Bruker-Michrom, Inc. (Auburn, Calif.). Trypsin (Trypsin Gold) was from Promega (Madison, Wis.). C-terminal isotopically labeled peptides containing U—$^{13}C_6$, U—$^{15}N_4$-arginine or U—$^{13}C_6$, U—$^{15}N_2$-lysine and unlabeled peptide standards were purchased from New England Peptide (Gardner, Mass.). Isotope labeled peptides were of greater than 99% and 95% isotopic and chemical purity, respectively; absolute concentration was determined by amino acid analysis.

Human Melanoma Biopsy Specimens—

Tissue sections (5 µm thickness) were obtained from archival FFPE tumor blocks from patients treated for melanoma at Vanderbilt University Medical Center. Participants all received immune checkpoint inhibitors as second or third line therapy. Samples were fixed in 10% buffered neutral formalin, processed and paraffin-embedded by standard methods in automated tissue processor. Five-µm sections were subjected to hematoxylin and eosin (H&E) staining and dual IHC using antibodies against PD-L1 (clone E1L3N, Cell Signaling Technology) and SOX10 (clone BC34, Biocare Medical). Sections analyzed by hematoxylin and eosin (H&E) staining and IHC were serially adjacent to those analyzed by MS.

IHC Analysis of PD-L1—

Tissue was incubated overnight at 4° C. with both rabbit monoclonal antibody against PD-L1 (clone E1L3N, Cell Signaling Technology, Catalog #13684, 1:100 dilution) and mouse monoclonal antibody against SOX-10 (clone BC34, Biocare, dilution 1:200). Antigen retrieval was performed using Citrate Buffer pH6 (Biocare Dechloaking Chamber). Visualization was preformed using MACH2 system (Biocare), DAB and Fast Red as chromogens, and counterstained with hematoxylin. The slides were scanned using a high resolution scanner (Leica SCN400 Slide Scanner) at 20× magnification. PD-L1 was scored and expressed as a percentage of stained cells for tumor cells, peri- and intra-tumoral immune infiltrate (mostly mononuclear phagocytic cells), and other non-tumor tissue cells.

Cell Culture and Preparation of Lysates—

HEK-293 cells (CRL-1573, ATCC) were grown in DMEM (Life Technologies, Carlsbad, Calif.) supplemented with 10% fetal bovine serum (Atlas Biologicals, Fort Collins, Colo.) at 37° C. in a humidified atmosphere with 5% $CO_2$. Cells were harvested, washed twice in phosphate-buffered saline, and frozen at 80° C. until used. Frozen cell pellets were lysed on ice in 8M urea supplemented with 1×HALT protease and phosphatase inhibitor (Life Technologies). Lysates were clarified by centrifugation at 10,000×g for 10 min at 4° C. and desalted with a Sep-Pak C18 1 cc Vac Cartridge (100 mg, 55-105 µm particle size (Waters, Milford, Mass.). Protein in the lysates was measured with the bicinchoninic acid (BCA) assay (Pierce, Rockford, Ill.).

Extraction and Digestion of Proteins from FFPE Melanoma Sections—

The material from two 5 µm FFPE tissue sections was scraped from the glass slides using a clean razor blade and transferred into a clean 1.5 mL Eppendorf tube. FFPE tissue was de-paraffinized and hydrated using procedures well known in the art. After hydration, the proteins were re-suspended in 100 µL of 100 mM ammonium bicarbonate, pH 8.0 (AmBic). Proteins were extracted from the rehydrated specimens by a two-step procedure. First, 100 µL of trifluoroethanol was added to each sample, followed by the addition of 100 µL of AmBic. Each tube was sonicated 3 times continuously for 20 s using a Sonic Dismembrator probe at level 2 (Model 100, Fisher Scientific, Waltham, Mass.), with cooling of samples on ice for 30 seconds between each sonication step. Samples then were gently shaken for 60 min at 60° C. For the second extraction step, 100 µL of 10M urea was added to each tube and sonication steps, described above, were repeated. Samples then were gently shaken for 60 min at 60° C. Protein concentration in lysates was measured using the BCA assay (ThermoFisher Scientific, Waltham, Mass.).

For protein cleavage by protease digestion, aliquots of lysate corresponding to 100 µg protein were diluted to a volume 200 µL with AmBic. A 50 mM solution of dithio-threitol, prepared in 50 mM Ambic, was added to a final concentration of 5 mM and solutions were incubated for 30 min at 60° C. Iodoacetamide (100 mM prepared in HPLC-grade water) was added to a concentration of 10 mM and the solution was incubated in the dark for 20 min at room temperature. Samples were diluted further with 800 µL of AmBic to achieve final concentrations of ≤10% trifluoroethanol and ≤1M urea before digestion. Trypsin (2 µg) was added to each sample to achieve a 1:50 (w/w) trypsin:protein ratio and the samples were incubated overnight at 37° C. After 16 h digestion, the samples were frozen at −80° C. and evaporated to dryness under vacuum.

Basic Reverse Phase Liquid Chromatography (bRPLC) Peptide Fractionation—

Dried sample residues were re-suspended in 350 µL deionized water and desalted with an Oasis HLB µElution Plate (30 µm particle size, Waters). Plates were pre-washed with 500 µL of acetonitrile and equilibrated with 750 µL of HPLC-grade water. The flow-through was discarded and the plates were washed with 500 µL of HPLC-grade water and the peptides were eluted with 80% acetonitrile. A mixture of 50 fmol each of the isotopically labeled peptide SID and LRP standards (see below) was added to each eluted peptide mixture. The tryptic peptides from the 100 μg digests then were fractionated using bRPLC separation with an Agilent 1260 Infinity HPLC System with a XBridge C18, 250 mm×4.6 mm analytical column (130 A, 5 μm particle size) and a XBridge C18 Sentry guard cartridge at a flow rate of 0.5 mL/min. The mobile phase consisted of 10 mM triethylamine bicarbonate pH 7.5 (TEAB) in water as solvent A and 10 mM TEAB in 90% acetonitrile as solvent B. The mobile phase was programmed from zero to 5% B in 5 minutes, from 5% to 35% B in 45 minutes and then held at 90% B for 10 minutes before returning to initial conditions. A total of 12 fractions were collected over time slices of 4.75 min each for the first 50 min of the program. The fractions were evaporated to dryness under vacuum and stored at −80° C. until PRM analysis.

Parallel Reaction Monitoring (PRM) Targeted MS—

PRM assays were performed on a Q Exactive Plus mass spectrometer (ThermoFisher Scientific, San Jose, Calif.) equipped with a Easy nLC1000 LC and autosampler system (ThermoFisher Scientific). For each analysis, 5 μL of each sample was injected onto a PicoFrit capillary column (New Objective, 30 cm×75 μm) packed ReproSil-Pur C18 AQ 3 μm resin (Dr. Maisch GmbH). Solvent A was 0.1% formic acid in water and solvent B was 0.1% formic acid in acetonitrile. Peptides were separated at a flow rate of 400 nL/min using a linear gradient of 2% solvent B for 1 min followed by increase to 28% solvent B over 48 min, then to 60% solvent B over 5 min, followed by an increase to 90% solvent B. The mobile phase was then held at that composition for 7 min before returning to initial conditions.

The acquisition method consisted of a full scan selected ion monitoring event followed by 14 targeted MS2 scans as triggered by a scheduled inclusion list, with a 5 minute retention time window containing the precursor m/z values. Retention times were determined from prior analyses of synthetic peptide standards. The MS1 scan was collected at a resolution of 17,5000, an automatic gain control (AGC) value of 3e6, a max injection time of 64 msec, and a scan range from m/z 380-1500. MS1 data were recorded in profile mode. The MS1 scan was followed by 14 targeted MS2 scans at a resolution of 70,000, an AGC value of 1e6, a max injection time of 240 msec, 0.7 m/z isolation window, fixed first mass of 200 m/z, an optimized collision energy for each target of 20, 23 or 27%. MS2 data were recorded in profile mode. Peptides targeted in the PRM analyses are provided in Table 1.

TABLE 1

| protein | bRPLC fraction | target peptide | SID std | LRP std | precursor m/z | CS [z] | NCE | MS/MS transitions, m/z |
|---|---|---|---|---|---|---|---|---|
| PD-L1 | F5 | VNAPYNK (light) (SEQ ID NO: 1) | | | 403.2138 | 2 | 27 | y2 (261.1557), y4 (521.2718), y5 (592.3089) |
| PD-L1 | F5 | VNAPYNK (heavy) (SEQ ID NO: 1) | x | x | 407.2209 | 2 | 27 | y2 (269.1697), y4 (529.2858), y5 (600.3229) |
| HAVCR2 (TIM3) | F5 | LANDLR (light) (SEQ ID NO: 2) | | | 351.2007 | 2 | 27 | y3 (403.2300), y4 (517.2729), y5 (588.3100) |
| PD-L1 | F6 | LQDAGVYR (light) (SEQ ID NO: 3) | | | 461.2431 | 2 | 27 | y4 (494.2722), y5 (565.3093), y6 (680.3362) |
| PD-L1 | F6 | LQDAGVYR (heavy) (SEQ ID NO: 3) | x | x | 466.2472 | 2 | 27 | y4 (504.2802), y5 (575.3173), y6 (690.3442) |
| LAG3 | F6 | LPAGVGTR (light) (SEQ ID NO: 4) | | | 385.7296 | 2 | 27 | y4 (432.2565), y6 (560.3151), y7 (657.3678) |
| CD40 | F6 | YC[+57]DPNLGLR (light) (SEQ ID NO: 5) | | | 554.2662 | 2 | 20 | y5 (572.3515), y7 (784.4312), y8 (944.4404) |
| PD-1 | F7 | LAAFPEDR (light) (SEQ ID NO: 6) | | | 459.7376 | 2 | 27 | y4 (516.2413), y6 (734.3468), y7 (805.3839) |
| PD-1 | F7 | LAAFPEDR (heavy) (SEQ ID NO: 6) | x | | 464.7418 | 2 | 27 | y4 (526.2493), y6 (744.3548), y7 (815.3919) |
| VISR (VISTA, C10orf54) | F8 | HPLSYVAQR (light) (SEQ ID NO: 7) | | | 535.7907 | 2 | 20 | y5 (636.3464), y7 (836.4625), y8 (933.5152) |
| CD3G | F8 | WNLGSNAK (heavy) (SEQ ID NO: 8) | x | | 449.2371 | 2 | 20 | y5 (484.2603), y6 (597.3444), y7 (711.3873) |

TABLE 1-continued

| protein | bRPLC fraction | target peptide | SID std | LRP std | precursor m/z | CS [z] | NCE | MS/MS transitions, m/z |
|---|---|---|---|---|---|---|---|---|
| PD-L2 | F9,10,11* | TPEGLYQVTSVLR (light) (SEQ ID NO: 9) | | | 731.8986 | 2 | 27 | y7 (802.4781), y8 (965.5415), y10 (1135.6470) |
| PD-L2 | F9,10,11* | TPEGLYQVTSVLR (heavy) (SEQ ID NO: 9) | x | | 736.9028 | 2 | 27 | y7 (812.4861), y8 (975.5495), y10 (1145.6550) |
| IDO1 | F9,10,11* | YILIPASQQPK (light) (SEQ ID NO: 10) | | | 629.3637 | 2 | 20 | y7 (755.4046), y8 (868.4887), y9 (981.5728) |
| CD4 | F9,10,11* | ILGNQGSFLTK (heavy) (SEQ ID NO: 11) | | x | 593.3395 | 2 | 20 | y6 (660.3805), y9 (959.5034), y10 (1072.5875) |
| PD-L1 | F12 | LFNVTSTLR (light) (SEQ ID NO: 12) | | | 525.8007 | 2 | 20 | y5 (577.3304), y6 (676.3988), y7 (790.4417) |
| PD-L1 | F12 | LFNVTSTLR (heavy) (SEQ ID NO: 12) | x | | 530.8049 | 2 | 20 | y5 (587.3384), y6 (686.4068), y7 (800.4497) |
| PD-L1 | F12 | LFDVTSTLR (light) (SEQ ID NO: 13) | | | 526.2928 | 2 | 20 | y5 (577.3304), y6 (676.3988), y7 (791.4258) |
| PD-L1 | F12 | LFDVTSTLR (SEQ ID NO: 13) (heavy) | x | | 531.2969 | 2 | 20 | y5 (587.3384), y6 (686.4068), y7 (801.4338) |
| PDL1-Glyc | F12 | LFN(glyco)VTSTLR (SEQ ID NO: 14) | | | 1134.0122 | 2 | 27 | 1253.672 (major fragment for all glycoforms) |

*these 3 fractions were combined for PRM analysis

Stable Isotope Dilution (SID) Analysis of PD-1, PD-L1 and PD-L2 Peptides—

Information on peptides and labeled standards representing PD-1, PD-L1, and PD-L2, including bRPLC fractions, precursor m/z, charge state, normalized collision energy and PRM transitions extracted is presented in Table 1. Reverse calibration curves were generated for each peptide pair by spiking a constant level of 2.5 fmol/µl of light peptide and heavy peptide standard at concentrations from a low value of 0.01562 fmol/µl to a high value of 10 fmol/µl in 56 µg/µl HEK-293 lysate background. Linearity of calibration curves was assessed and an equation for determining the analyte concentration using the peak area ratio of light/heavy isotopologs was defined using QuaSAR, which was implemented through the Skyline interface. The lower limit of quantitation (LLOQ) and the lower limit of detection (LLOD) for each peptide also were calculated with QuaSAR. PRM transitions were extracted from raw datafiles and analyzed with Skyline. Peptide peak areas were calculated as the sum of three most abundant transitions.

Labeled Reference Peptide (LRP) Analysis of IDO1, LAG3, HAVCR2 (TIM-3), VISR (VISTA, C10orf54) and CD40 Peptides—

Information on peptides and LRP standards representing IDO1, LAG3, HAVCR2 (TIM-3), VISR (VISTA, C10orf54) and CD40, including bRPLC fractions, precursor m/z, charge state, normalized collision energy and PRM transitions extracted is presented in Table 1. PRM transitions were extracted with Skyline and peak areas for the target peptides were normalized to the peak areas for isotope labeled standard peptides that were contained in the same bRPLC fractions as the target peptides. The ratio of target peptide peak area to LRP peptide peak area was used to compare abundances of the target peptides across the sample set.

Analysis of PD-L1 N-Linked Glycopeptides—

Recombinant human PD-L1 was reduced, alkylated and cleaved by trypsin digestion as described above. The digest (100 m) was treated with 1 µl of protein N-glycanase F (PNGase F; Promega, Madison, Wis., USA) in 25 µL AmBic, with incubation overnight at 37° C. The PD-L1 N-linked site was identified based on the difference in mass (0.98 Da) from the native sequence associated with conversion of the asparagine glycosylation site to aspartate after PNGase F treatment.

Structures of the intact N-linked glycopeptides in the tryptic digest of recombinant human PD-L1 and FFPE melanomas were manually interpreted from their MS/MS spectra. The chromatographic retention of heterogeneous N-linked glycopeptides is similar to that of the corresponding unmodified peptide in reverse phase chromatography, because the primary stationary phase interaction is with the hydrophobic peptide backbone. Accordingly, PD-L1 tryptic peptides and their glycopeptides eluted in the same bRPLC fraction and eluted closely in reverse phase LC-MS/MS analyses. The structures of intact N-linked glycopeptides were manually characterized with glycosidic MS/MS product ions and low molecular weight oxonium maker ions such as m/z 163 (Hex+), m/z 204 (HexNAc+), m/z 366 (Hex- HexNAc+), and m/z 292 (NeuNAc+). Only peak assignments with mass accuracy within 10 ppm of theoretical m/z were accepted for manual characterization.

Structures of the intact N-linked glycopeptides were initially identified by untargeted MS/MS analyses of the tryptic digest of recombinant human PD-L1. The chromatographic retention of heterogeneous N-linked glycopeptides is similar to that of the corresponding unmodified peptide in reverse phase chromatography, because the primary stationary phase interaction is with the hydrophobic peptide backbone. Accordingly, PD-L1 tryptic peptides and their glycopeptides eluted in the same bRPLC fraction and eluted closely in reverse phase LC-MS/MS analyses. Possible glycan structures for N-glycosylated peptides were identified from MS1 data with the GlycoMod tool (web.expasy.org/glycomod/). The structures of N-linked glycopeptides from both recombinant PD-L1 and from melanoma specimens were manually characterized from MS/MS spectra. Only peak assignments with mass accuracy within 10 ppm of theoretical m/z were accepted for manual characterization.

Statistical Design and Experimental Rationale—

Analyses of the recovery of PD-L1 peptides LQDAGVYR (SEQ ID NO:3) and VNAPYNK (SEQ ID NO:1) from recombinant PD-L1 protein spiked into HEK-293 cell lysates were done in duplicate. Analyses of the reproducibility of measurement of peptides from PD-1, PD-L1 and PD-L1 were done with four full process replicates. Because of limiting amounts of available samples, a single protein preparation and tryptic digest was fractionated for each melanoma sample and each bRPLC fraction was analyzed once by targeted MS. Calibration curves were analyzed with the QuaSAR utility as implemented in Skyline and QuaSAR was used to determine LLOD and LLOQ. MS-measured abundances of PD-1, PD-L1, and PD-L2 peptides were compared by Pearson correlation with a two-tailed t-test for significance. MS and IHC-measured abundances of PD-L1 were compared by Spearman rank correlation with a two tailed t-test for significance.

Figure 7:
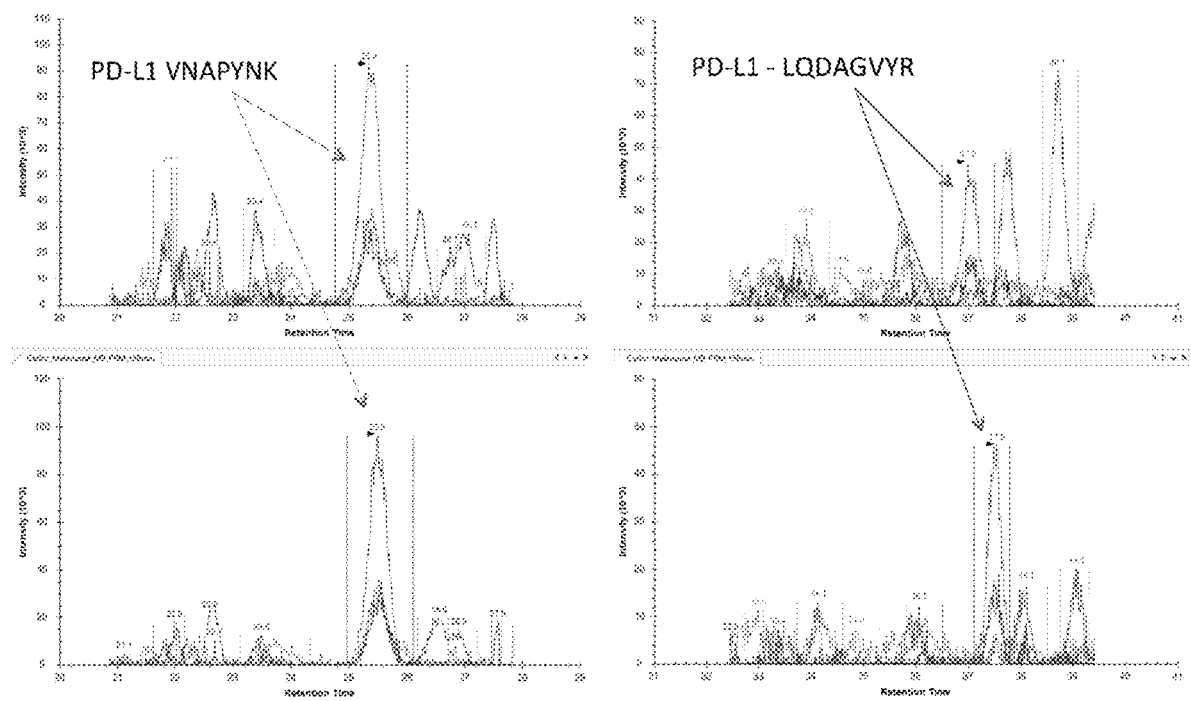
FIG. 7 shows detection of PD-L1 peptides in long gradient LC-PRM analyses of unfractionated digests from formalin-fixed, paraffin-embedded (FFPE) melanomas.
Figure 8:
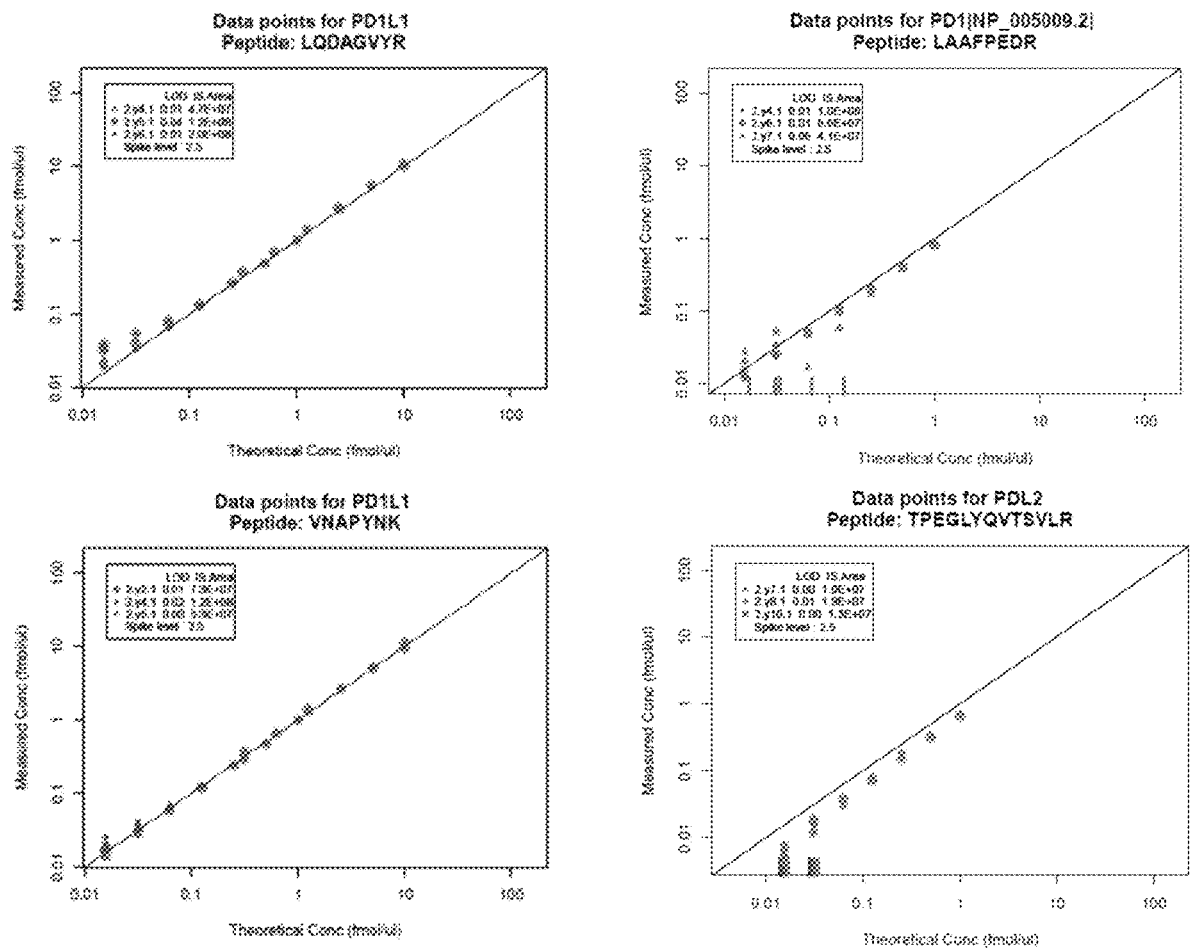
FIG. 8 shows stable isotope dilution (SID) calibration curves for PD-1L1 LQDAGVYR peptide (upper left panel), PD-1L1 VNAPYNK peptide (lower left panel), PD-L2 LAAFPEDR peptide (upper right panel), and PD-L2 TPEGLYQVTSVLR peptide (lower right panel).

Example 2: Optimization of an Addressable Fractionation PRM Assay for PD-1, PD-L1, and PD-L2 and Other Immune Checkpoint Proteins Initial analyses of FFPE melanoma sections employed a single long gradient (150 min) run of unfractionated tryptic digest. These analyses detected PD-L1 proteotypic peptides VNAPYNK (SEQ ID NO:1) and LQDAGVYR (SEQ ID NO:3), but with low signal intensity, which would likely be inadequate for robust quantitation (FIG. 7). To improve assay sensitivity, an addressable basic reverse phase fractionation (bRPLC) strategy was developed. Unlabeled peptide standards of moderate (~85%) purity were used to establish the elution "address" for each peptide in 12 bRPLC fractions. For most peptides, the majority of detectable signal eluted in a single bRPLC fraction. The list of proteins, peptides and their corresponding bRPLC fractions is presented in Table 1. Once the fraction addresses for all peptides were established, it was possible to configure assays for specific targets and combinations by selecting the corresponding bRPLC fractions for PRM analysis. To minimize effects of sample loss during fractionation, SID standards were spiked into tryptic digests immediately prior to bRPLC fractionation. For PD-1, PD-L1, and PD-L2, preliminary analyses of several target peptides and corresponding SID standards identified a set of four peptides without significant interferences in FFPE melanomas and with robust, linear calibration curves for standards spiked into HEK-293 cell lysates. Calibration curves are shown in FIG. 8.

Figure 9:
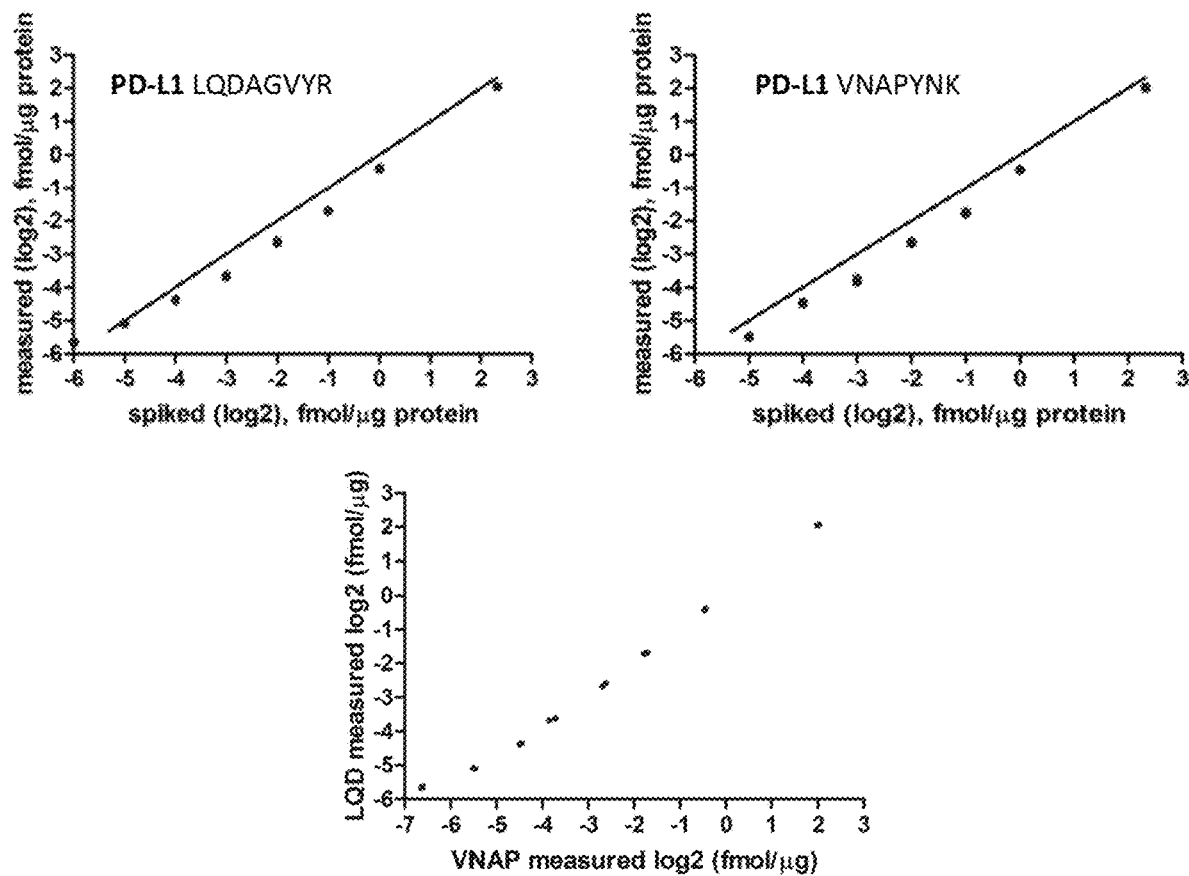
FIG. 9 shows spike recovery for recombinant human PD-L1 in 100 µg HEK293 cell lysate. Recombinant human PD-L1 protein was spiked at 0, 0.031, 0.063, 0.125, 0.25, 0.50, 1.00, or 5.00 fmol (LQDAGVYR peptide, upper left panel; VNAPYNK peptide, upper right panel; VNAP peptide, bottom middle panel). Duplicate response curves for both peptides were linear across the spike range with slopes of unity, which corresponded to approximately 100% recovery

To estimate the spike recovery of the SID assays for PD-L1 peptides VNAPYNK (SEQ ID NO:1) and LQDAGVYR (SEQ ID NO:3), recombinant human PD-L1 protein was spiked at 0, 0.031, 0.063, 0.125, 0.25, 0.50, 1.00, or 5.00 fmol in 100 μg HEK-293 cell lysate. Duplicate response curves for both peptides were linear across the spike range with slopes of unity, which corresponded to approximately 100% recovery (FIG. 9). The peptides VNAPYNK (SEQ ID NO:1) and LQDAGVYR (SEQ ID NO:3) were released from PD-L1 in a 1:1 ratio, as indicated by Pearson correlation (r=1.000) for their yields in the spike-recovery experiments. Four full process replicate analyses of a single FFPE melanoma specimen were then performed. Coefficients of variation for the measurements were 6.6% (VNAPYNK (SEQ ID NO:1); PD-L1), 5.8% (LQDAGVYR (SEQ ID NO:3); PD-L1), 10.9% (TPEG-LYQVTSVLR (SEQ ID NO:9); PD-L2) and 20.1% (LAAF-PEDR (SEQ ID NO:6); PD-1). Data are shown in Table 2 below.

TABLE 2

|      | PDL1-VNA | PDL1-LQD | PDL2-TPE | PD1-LAA |
|------|----------|----------|----------|---------|
| R1   | 0.435    | 0.744    | 1.9      | 0.0342  |
| R2   | 0.415    | 0.732    | 1.95     | 0.0451  |
| R3   | 0.387    | 0.69     | 1.57     | 0.0565  |
| R4   | 0.377    | 0.795    | 2.03     | 0.0489  |
| mean | 0.4035   | 0.74025  | 1.8625   | 0.046175 |
| SD   | 0.026451 | 0.043223 | 0.202217 | 0.009284 |
| CV   | 0.065554 | 0.05839  | 0.108573 | 0.201065 |
| LOD  | 0.003536 | 0.011774 | 0.007982 | 0.008952 |
| LOQ  | 0.010609 | 0.035322 | 0.023946 | 0.026855 |

Example 3: Histologic and IHC Analysis of PD-L1 in Human FFPE Melanomas

Twenty-two sections of FFPE melanoma tissue from biopsies or surgical resections were obtained from patients treated with immune checkpoint inhibitors. Although clinical outcome information is available for these individuals, the cohort does not correspond to a clinical trial and is not designed to test hypotheses linking molecular features to outcomes. The specimens represented multiple tissue sites typically encountered in diagnosis and therapeutic assessment of melanoma. The specimens included primary skin tumors and lung, intestinal, lymph node and other metastases. The specimens also varied in morphology and cellular composition.

IHC analyses were performed with the anti-PD-L1 antibody E1L3N, which recognizes an intracellular PD-L1 epitope near the PD-L1 C-terminus. IHC detected PD-L1 immunoreactivity in tumor cells, histiocytes, and t issue macrophages, as well as in peripheral nerves, ganglion cells, skeletal muscle, intestinal epithial cells and salivary epithelial cells. The cellular composition of the samples and the fractions of each cell type component that stained positive for PD-L1 are represented in FIG. 1. The cell types represented are tumor cells, inflammatory infiltrate (mostly mononuclear phagocytic cells including histiocytes, macrophages, and dendritic cells) and other cell types and where solid coloring indicates the PD-L1 positive fractions. Estimates for all cell types in each sample are presented in Table 3 below. In some samples, most of the PD-L1-positive staining was in tumor cells (e.g., B10 and B29), whereas in others PD-L1 positive staining was primarily in lymphocytes or histiocytes (B1, B25) or in other cells, such as alveolar macrophages and skeletal muscle (B7 and B8).

TABLE 3

| Sample Identifier | % Tumor cells whole section | % PD-L1+ Tumor cells | % lymphocytes whole section | % PD-L1+ lymphocytes (histiocytes) | % other cells/ whole section | % PD-L1+ other cells | % PD-L1+ total section | Other cell types PD-L1+ | Site | Notes |
|---|---|---|---|---|---|---|---|---|---|---|
| B1 | 2 | 0 | 85 | 30 | 13 | 40 | 31 | histiocytes and dendritic cells | Lymph node | Lymph node with metastasis: Histiocytes express PD-L1 around the metastasis and in all lymph node. |
| B2 | 65 | 0 | 30 | 25 | 5 | 0 | 8 | histiocytes and dendritic cells | Lymph node | Lymph node metastasis |
| B4 | 70 | 0 | 9 | 5 | 19 | 10 | 2 | hystiocytes and peripheral nerves and ganglion cells | Small intestine | Small intestine mestastasis: tumor with extensive necrosis. Normal intestines histiocytes and ganglion (nervous) cells express PD-L1 |
| B5 | 40 | 5 | 6 | 30 | 54 | 2 | 5 | skeletal muscle | Skin | Primary tumor (Skin) |
| B7 | 25 | 0 | 18 | 0 | 53 | 10 | 5 | alveolar macrophages | Lung | Lung metastasis |
| B8 | 40 | 0 | 4 | 0 | 56 | 20 | 11 | skeletal muscle | Skin | Primary tumor (Skin). Tumor consisting of spindle cells negative for PD-L1 |
| B9 | 90 | 0 | 6 | 0 | 4 | 0 | 0 | | Soft tissue (orbit) | Pleomorphic tumor. Almost no immune response. |
| B10 | 86 | 60 | 12 | 10 | 2 | 0 | 53 | | Bladder | Pleomorphic tumor |
| B11 | 85 | 25 | 15 | 15 | 0 | 0 | 24 | | Lymph node | Spindely tumor |
| B12 | 68 | 30 | 10 | 5 | 22 | 5 | 22 | alveolar macrophages | Lung | Lung metastasis. Tumor with necrosis. |
| B13 | 65 | 0 | 18 | 20 | 17 | 35 | 10 | intestinal epithelial cells, immune (histiocytes/ dendritic) cells and peripheral nerves and ganglion cells | Small intestine | Small intestine metastasis. Pleomorphic tumor. Normal intestines histiocytes and ganglion (nervous) cells express PD-L1 |
| B14 | 73 | 0 | 18 | 10 | 9 | 15 | 3 | immune (histiocytes/ dendritic) cells and peripheral nerves and ganglion cells | Small intestine | Small intestine metastasis. Normal intestines histiocytes and ganglion (nervous) cells express PD-L1 |

TABLE 3-continued

| Sample Identifier | % Tumor cells whole section | % PD-L1+ Tumor cells | % lymphocytes whole section | % PD-L1+ lymphocytes (histiocytes) | % other cells/ whole section | % PD-L1+ other cells | % PD-L1+ total section | Other cell types PD-L1+ | Site | Notes |
|---|---|---|---|---|---|---|---|---|---|---|
| B17 | 10 | 0 | 8 | 0 | 82 | 0 | 0 | | Lung | Lung metastasis: spindly tumor |
| B20 | 97 | 20 | 2 | 15 | 1 | 0 | 20 | | Soft tissue | Epithelioid tumor |
| B21 | 9 | 0 | 0 | 0 | 91 | 0 | 0 | | Skin | Primary tumor (skin) |
| B22 | 30 | 70 | 15 | 0 | 55 | 10 | 27 | alveolar macrophages | Lung | Lung metastasis. Tumor cells are very pleomorphic. |
| B23 | 50 | 0 | 17 | 30 | 33 | 15 | 10 | immune (histiocytes/ dendritic) cells and salivary epithelial | Pancreas | Salivary gland next to tumor. |
| B24 | 50 | 0 | 6 | 5 | 44 | 0 | 0 | immune (histiocytes/ dendritic) cells | Skin | Primary tumor (skin). Tumor necrosis. |
| B25 | 70 | 5 | 20 | 70 | 10 | 0 | 18 | | Soft tissue (mediastinum) | Tumor with necrosis |
| B26 | NA* | NA | NA | NA | NA | NA | NA | | Soft tissue (pericolonic) | Epithelioid tumor |
| B28 | 25 | 0 | 6 | 2 | 69 | 0 | 0 | | Skin | Primary tumor (skin) |
| B29 | 85 | 70 | 12 | 10 | 3 | 0 | 61 | | Lymph node | Spindely tumor |

Example 4: MS Analysis of PD-L1, PD-1, and PD-L2

Figure 2:
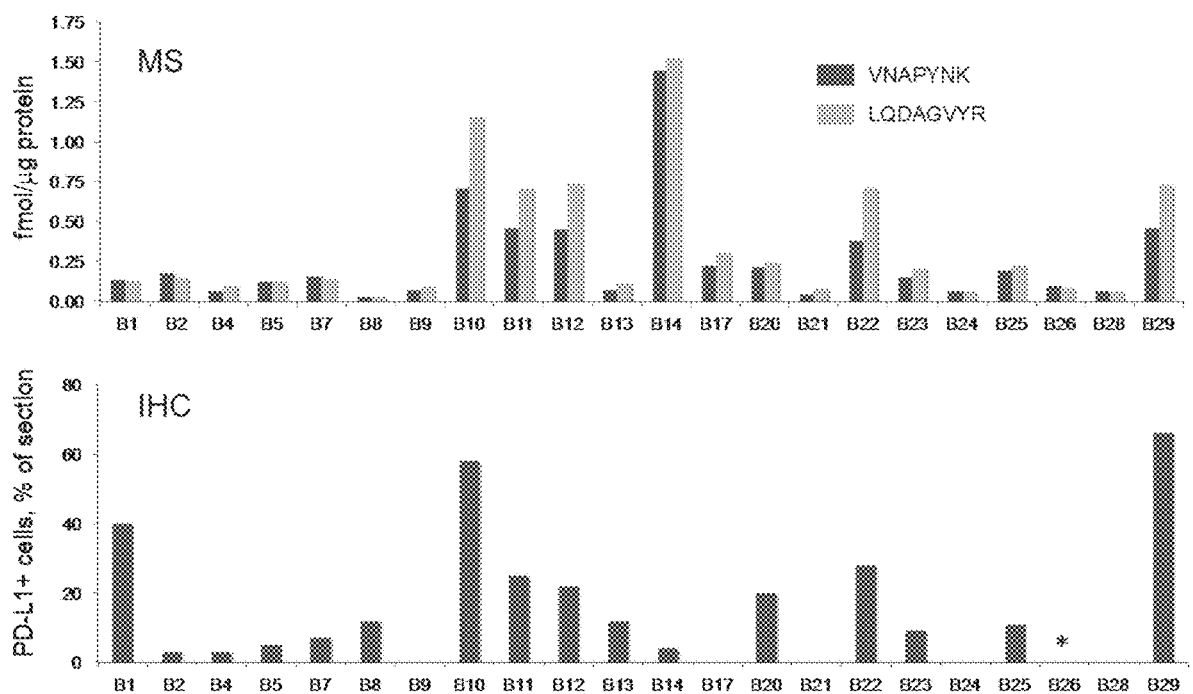
FIG. 2 shows a comparison of PD-L1 abundance in 22 melanoma samples by MS (upper panel) and IHC (lower panel). MS measurements for PD-L1 peptides LADAGVYR (SEQ ID NO:15) and VNAPYNK (SEQ ID NO:1) are shown in fmol/µg protein. IHC measurements indicate percentage PD-L1 positive cells among all cells in each section.

PD-L1 was measured via SID assays for the peptides VNAPYNK (SEQ ID NO:1) and LQDAGVYR (SEQ ID NO:3), as described above (FIG. 2). Measurements for both peptides were above the lower limit of quantitation (LLOQ) in all samples and ranged 50-fold, from approximately 0.03 to 1.5 fmol/μg protein. VNAPYNK (SEQ ID NO:1) and LQDAGVYR (SEQ ID NO:3) measurements were highly correlated ($r^2$=0.9161, p<0.0001), but VNAPYNK (SEQ ID NO:1) was often measured at lower abundance (mean 0.85±0.22). This may reflect variable loss of the lysine C-terminal peptide VNAPYNK (SEQ ID NO:1) due to formalin fixation. Nevertheless, the two peptides provide consistent measurements of PD-L1 abundance differences across the sample set.

A comparison between the MS and IHC results was conducted. MS measures molar quantities of PD-L1, whereas IHC measures percentages of cells in a field that exceed a minimum threshold staining intensity. Percentages of cells that exceed the threshold may be proportional to the overall molar amount of PD-L1 in a sample. Comparison of the PD-L1 abundances measured by MS with total cellular PD-L1 (FIG. 2) detected by IHC indicated a significant correlation between the platforms (Spearman r=0.5841, p=0.0054). A notable outlier was sample B14 (from a small intestinal metastasis), which indicated little PD-L1 by IHC (3% of entire section), but the highest MS-measured PD-L1 abundance of all the samples.

Cells that exceed a staining intensity threshold by IHC analysis may contain substantially different amounts of PD-L1. For example, sample B29 had the highest PD-L1 positive percentage of cells (61%), but had only the fourth highest PD-L1 MS measurement. Similarly, sample B1 had the 3$^{rd}$ highest IHC rank, with 31% PD-L1 positive cells, but was the 13$^{th}$ highest MS rank for PD-L1 abundance. Sample B29 displayed low intensity staining across the tumor cells, whereas sample B1 displayed small numbers of intensely stained cells in a background of low staining intensity. Thus, although IHC can distinguish tissues with PD-L1 staining above or below a threshold, IHC is nevertheless a poor measure of PD-L1 quantity in tissues.

A key difference between the IHC and MS platforms is that only IHC enables assignment of PD-L1 staining to specific cell types in a section. PD-L1 staining was found in multiple cell types, including tumor cells, histiocytes, macrophages, skeletal muscle, epithelia, and nerve cells. The cell types displaying PD-L1 positive staining also varied considerably. For example, samples B10, B11, B12, B20, and B29 all had >65% tumor cells, which accounted for almost all of the PD-L1 positive staining. Samples B1 and B2, both from lymph node metastases, displayed PD-L1 positive staining principally in lymphocytes and histiocytes. In samples B7 (lung metastasis) and B8 (primary tumor), PD-L1 positive staining was localized to macrophages and skeletal muscle, respectively. Comparison of the IHC and MS data indicates that the highest MS measurements usually corresponded to samples with a significant fraction of PD-L1 positive tumor cells. As such, the cellular source of MS-measured PD-L1 cannot be assigned to any particular cell type without accompanying IHC measurement.

Figure 3:
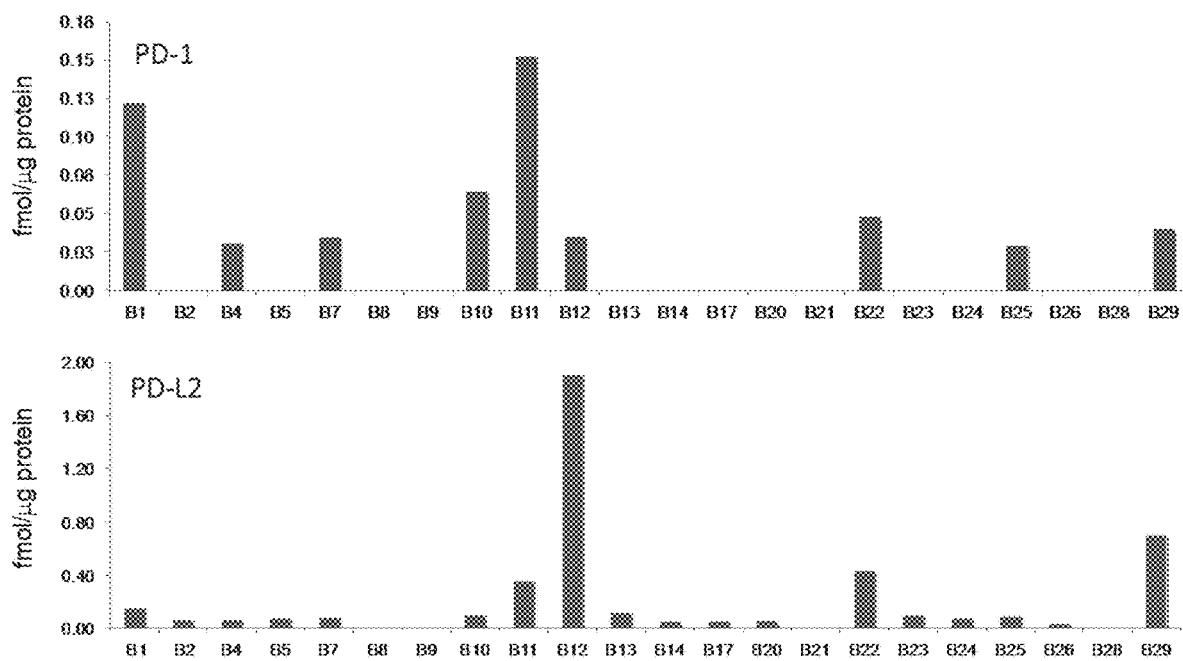
FIG. 3 shows PD-1 (upper panel) and PD-L2 (lower panel) abundance in 22 melanoma samples measured by MS.

PD-1 was quantifiable via the peptide LAAFPEDR (SEQ ID NO:6) in 9 of the 22 samples and measured values ranged 5-fold from 0.03 to 0.15 fmol/m protein (FIG. 3). PD-1 abundance was weakly correlated ($r^2$=0.3057, p=0.009) with the fraction of lymphocytes/histiocytes in sections. PD-L1 abundance was up to 20-fold greater than PD-1 abundance in samples where both were quantifiable (FIG. 4, but the abundances were not significantly correlated ($r^2$=0.062, p=0.264).

Figure 4:
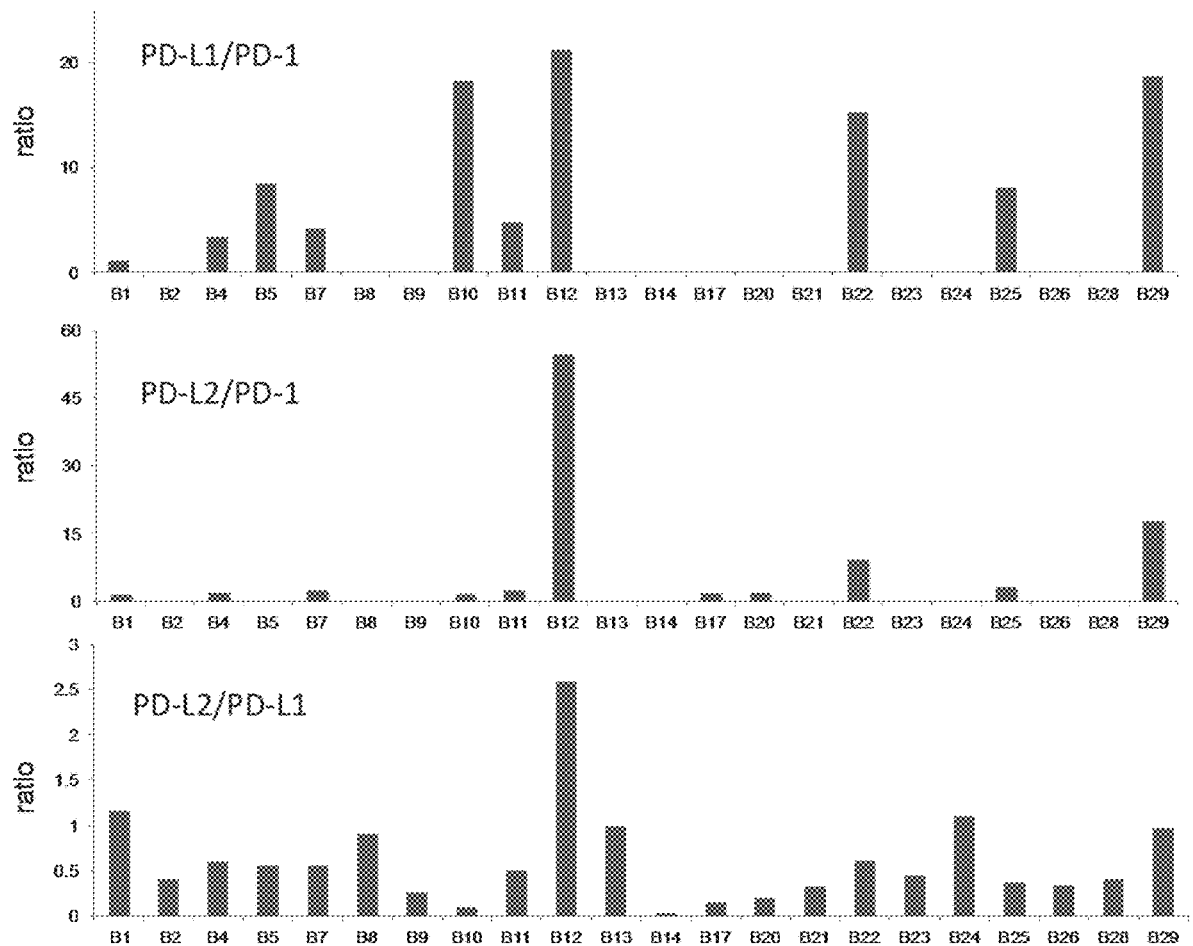
FIG. 4 shows abundance ratios for PD-L1:PD-1 (upper panel), PD-L2:PD-1 (middle panel) and PD-L2:PD-L1 (lower panel) in 22 melanoma samples measured by MS. Ratios are presented only for samples in which both proteins were quantifiable above the lower limit of quantitation (LLOQ).

Targeted MS affords a systematic approach to develop assays for proteins for which high quality antibody reagents are unavailable. PD-L2 has been recognized as a regulator of PD-1 with higher affinity than PD-L1. However, PD-L2 displays low expression in solid tumors and lacks high quality antibodies for traditional quantification methods. MS measurements demonstrate PD-L2 expression in melanomas at levels comparable to PD-L1 (FIG. 3). PD-L2 was quantifiable via the peptide TPEGLYQVTSVLR (SEQ ID NO:9) in 18 of the 22 samples and measured values ranged 95-fold from 0.03 to 1.90 fmol/m protein (FIG. 3). The ratio of PD-L2 to PD-L1 abundance ranged from 0.03 to 2.58 (FIG. 4). PD-L2 was more abundant than PD-L1 in sample B12, was at equal abundance with PD-L1 in five other samples and was at least half the level of PD-L1 in half of the entire sample set (FIG. 4). PD-L2 and PD-L1 abundances were not significantly correlated ($r^2$=0.118, p=0.1169). Given that PD-L2 binds PD-1 with 2-6-fold higher affinity than does PD-L1, these data suggest that PD-L2 is present in sufficient abundance to contribute to PD-1-dependent T-cell down-regulation. PD-L2-dependent effects thus may impact the responsiveness of cancers to immune checkpoint therapeutics, particularly for drugs directed against PD-L1. Both PD-L1 and PD-L2 were more abundant than PD-1 in all samples for which abundance ratios could be measured.

Example 5: MS Analysis of PD-L1 N-Glycosylation

Figure 10:
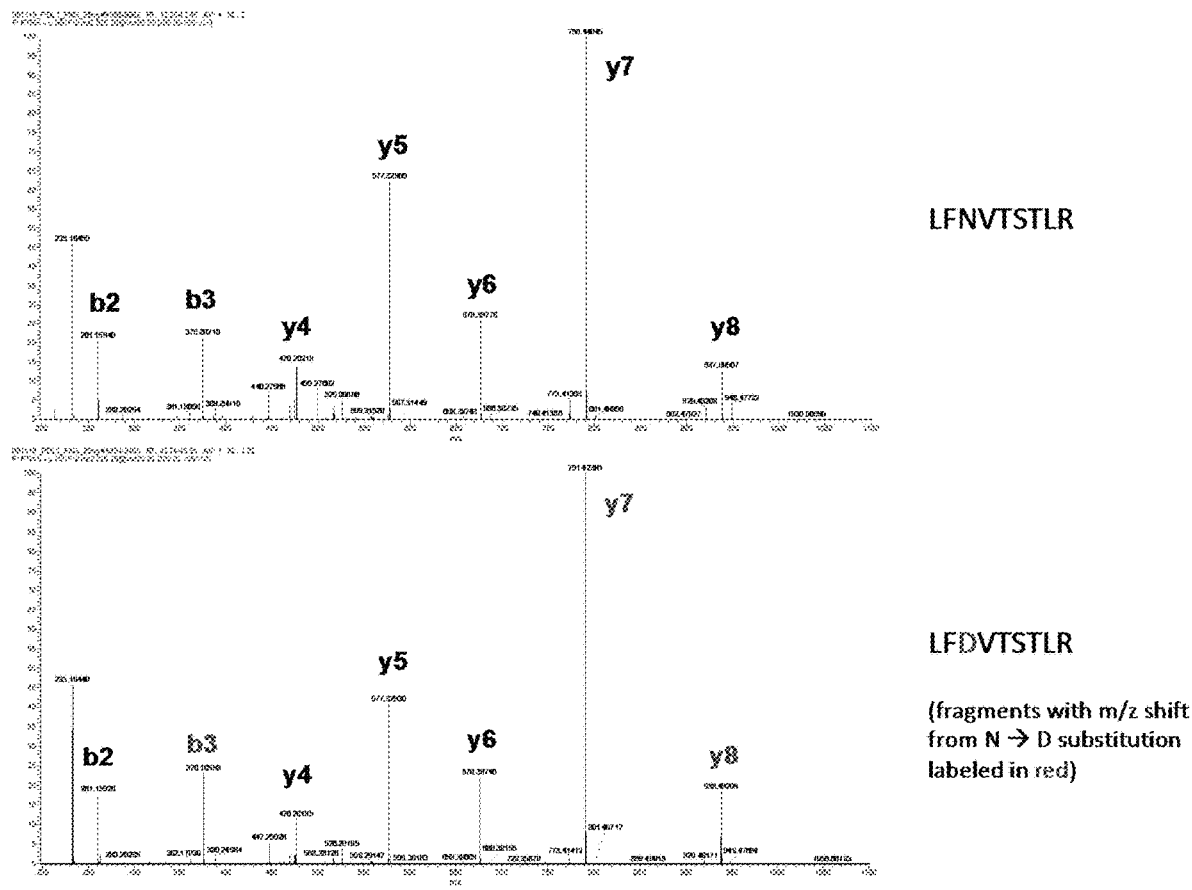
FIG. 10 shows tandem mass spectrometry (MS/MS) spectra of PD-L1 LFNVTSTLR (SEQ ID NO:12) peptide (top panel) and LFDVTSTLR (SEQ ID NO:13) peptide (bottom panel) released by PNGase F treatment of recombinant human PD-L1 tryptic digest. Fragments with m/z shift from N to D substitution are labeled in red.
Figure 11:
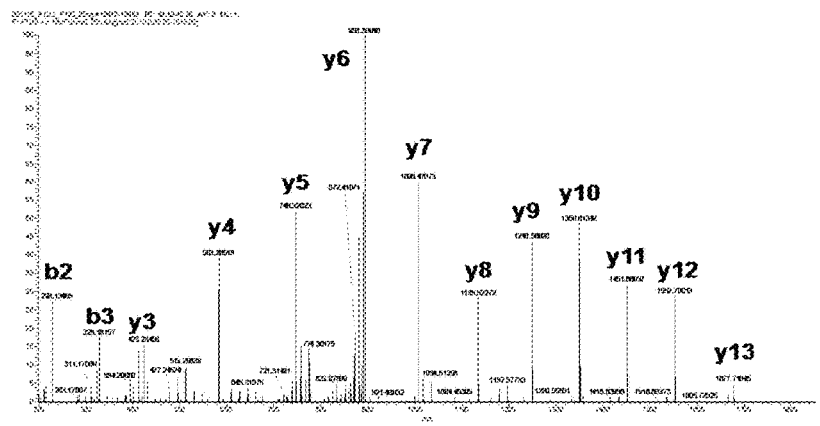
FIG. 11 shows MS/MS spectra of PD-L1 INTTTNEIFYCTFR (SEQ ID NO:16) peptide (top panel) and PD-L1 IDTTTNEIFYCTFR (SEQ ID NO:17) peptide (bottom panel) released by PNGase F treatment of recombinant human PD-L1 tryptic digest. Fragments with m/z shift from N to D substitution are labeled in red.
Figure 11:
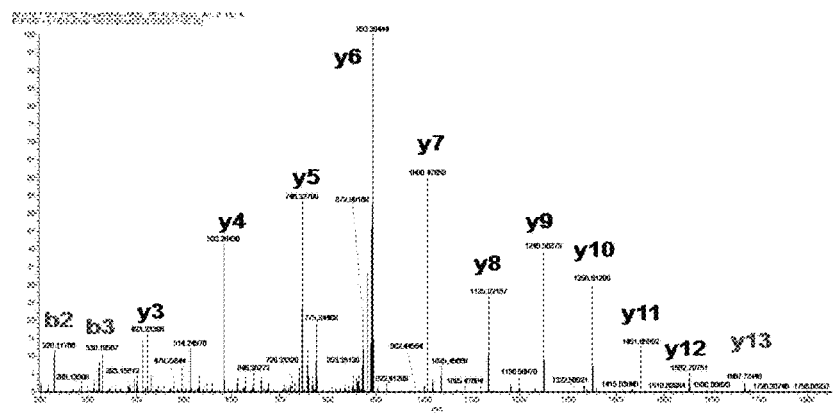
Figure 12:
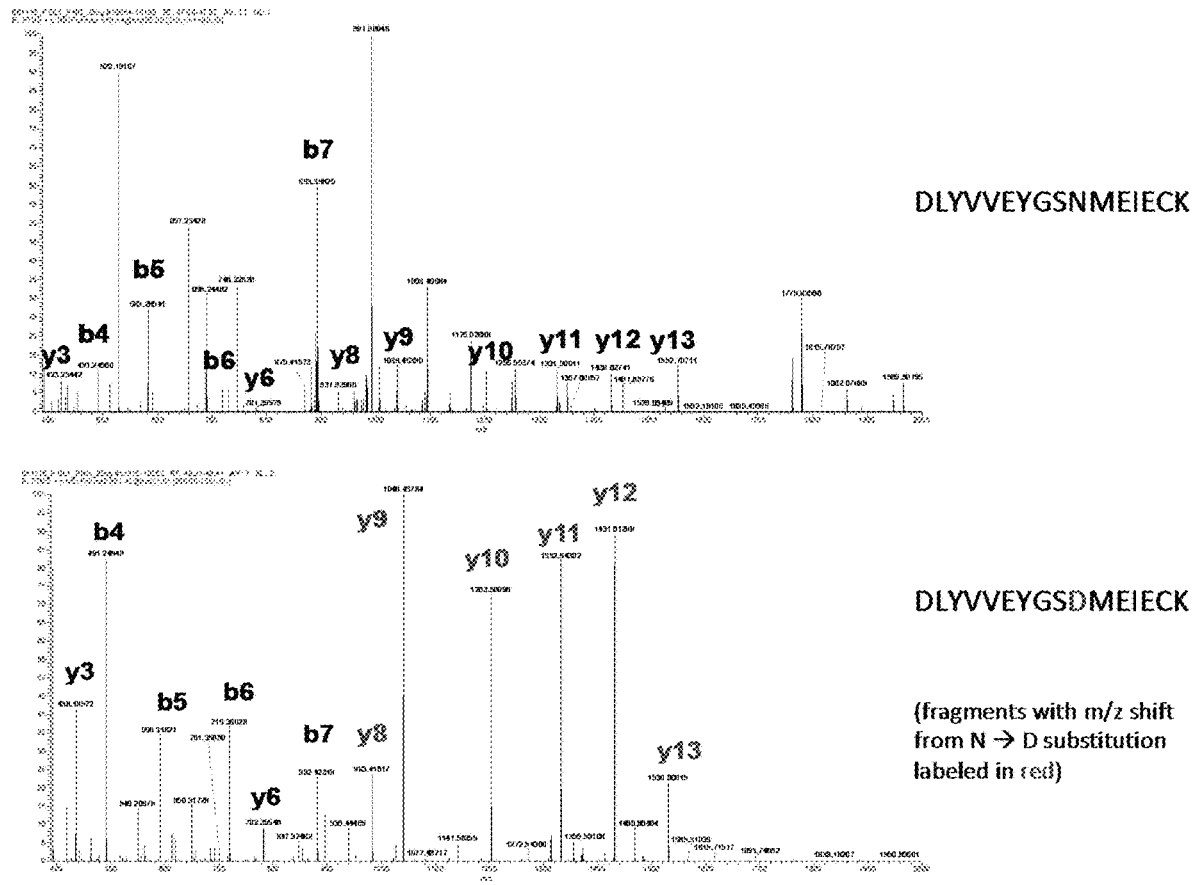
FIG. 12 shows MS/MS spectra of PD-L1 DLYVVEYGSNMEIECK (SEQ ID NO:18) peptide (top panel) and PD-L1 DLYVVEYGSDMEIECK (SEQ ID NO:19) peptide (bottom panel) released by PNGase F treatment of recombinant human PD-L1 tryptic digest. Fragments with m/z shift from N to D substitution are labeled in red.
Figure 13A:
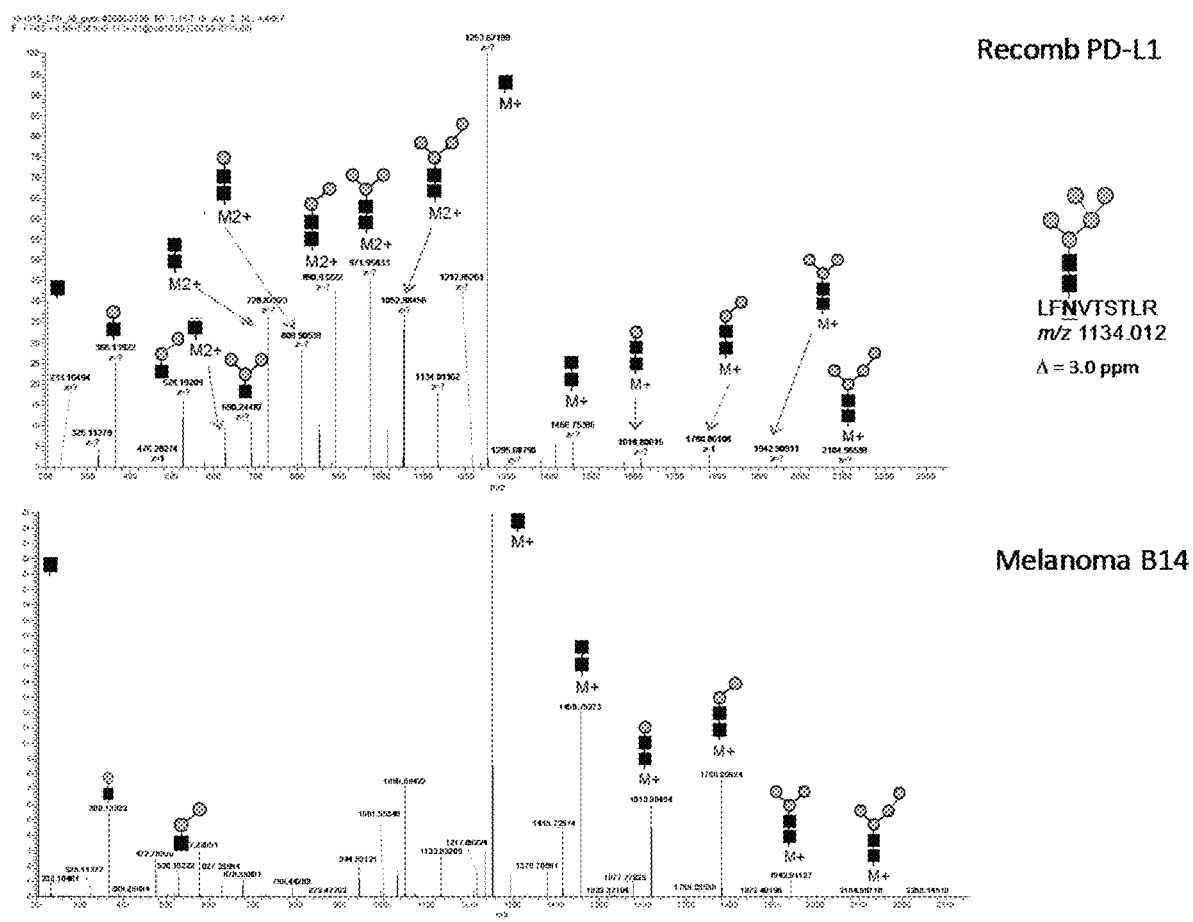
FIGS. 13A-13E show MS/MS analyses of tryptic N-glycopeptide forms of LFNVTSTLR (SEQ ID NO: 12) from the recombinant PD-L1 protein (top panel) and the melanoma specimen B14 (bottom panel).
Figure 13B:
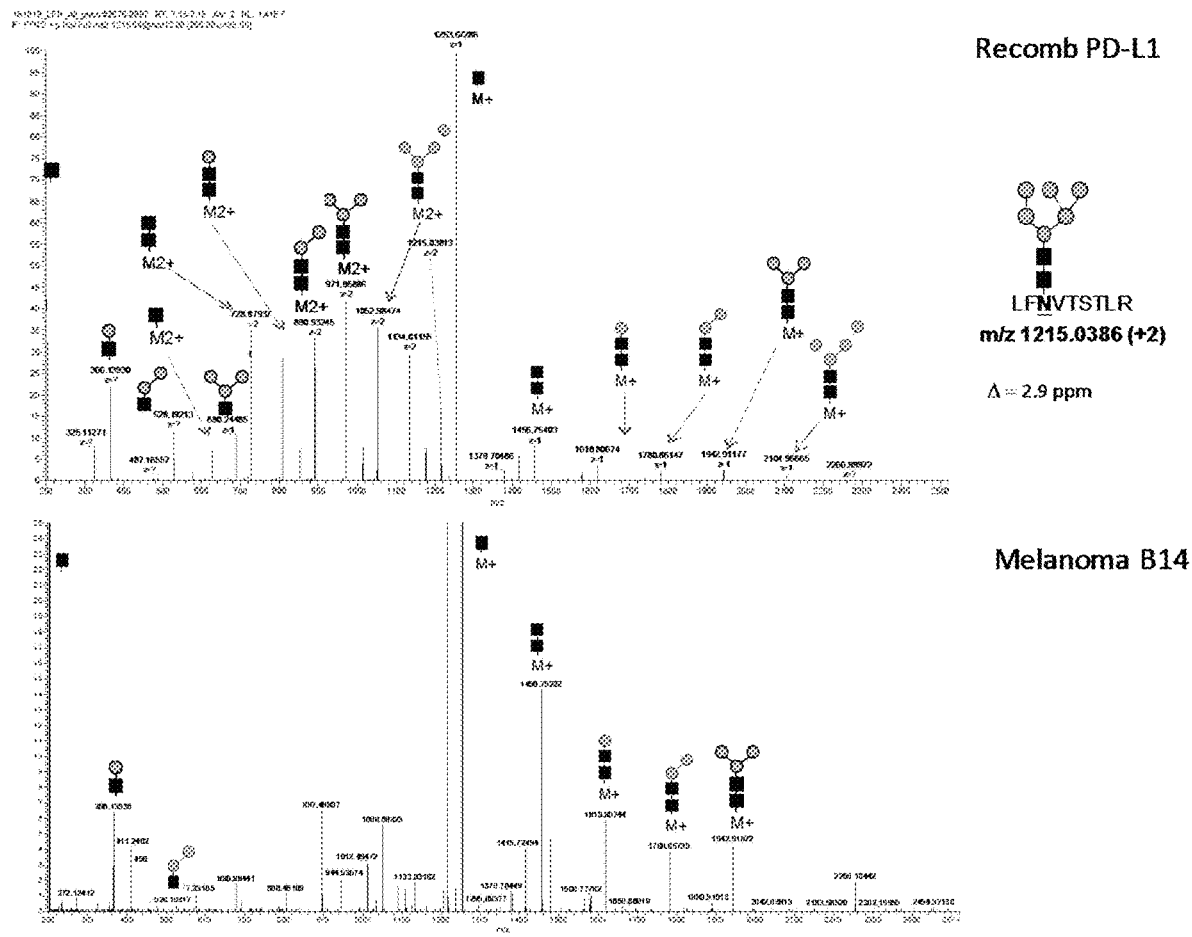
Figure 13C:
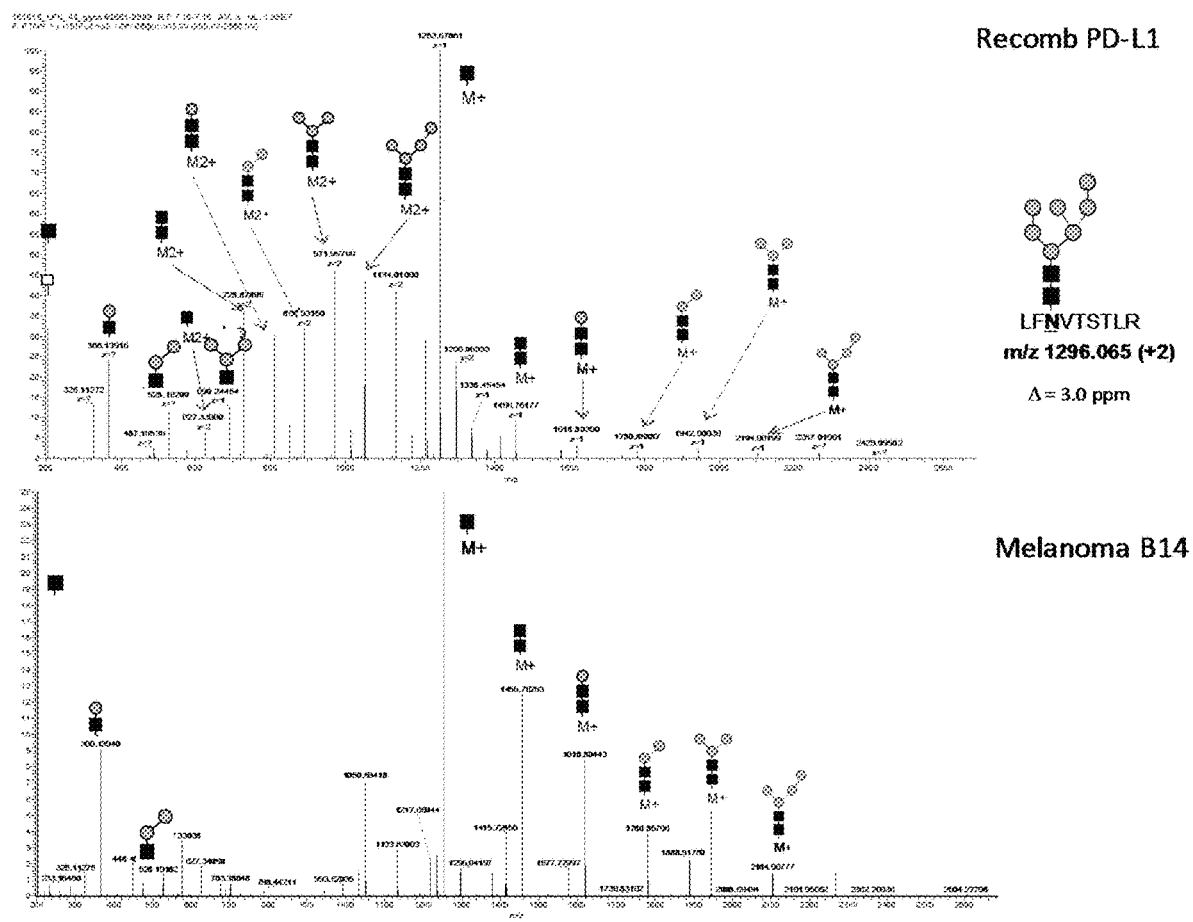
Figure 13D:
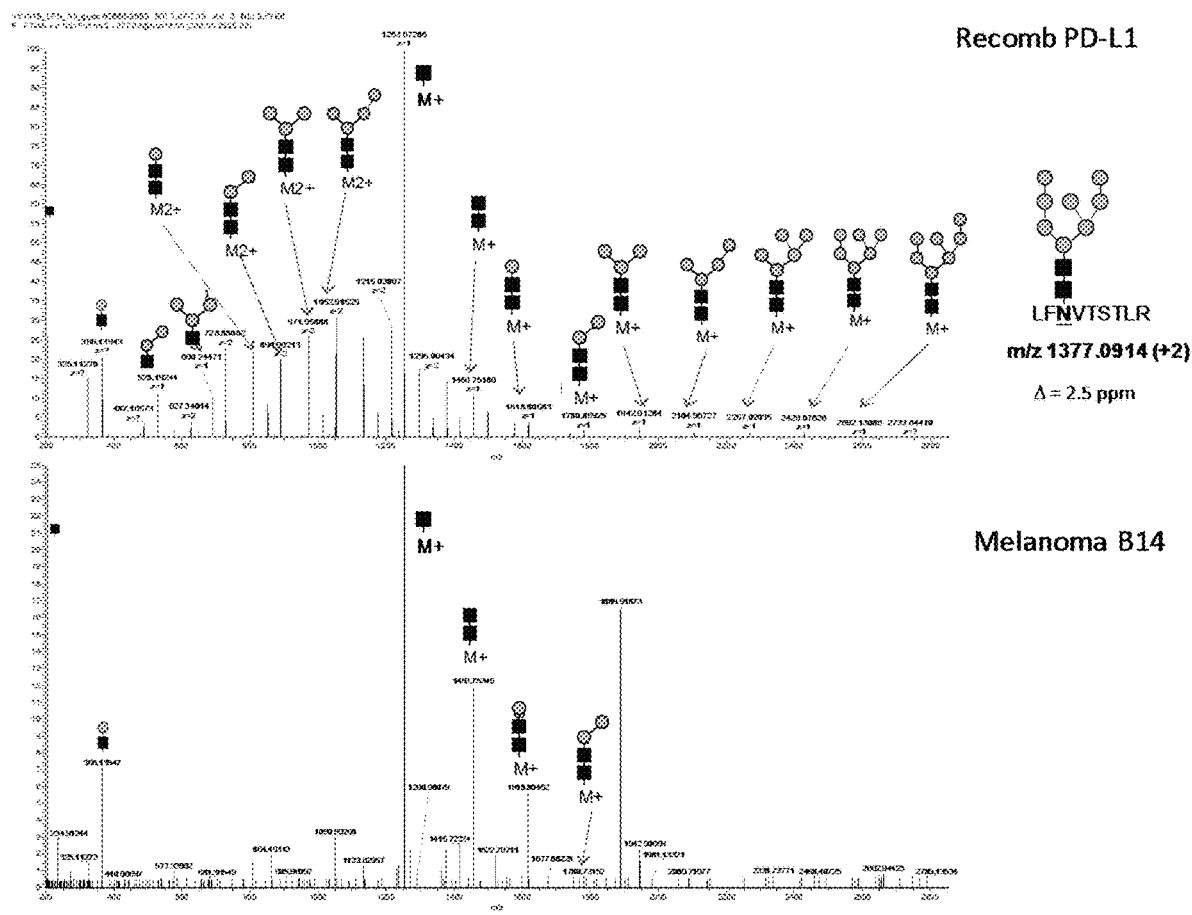
Figure 13E:
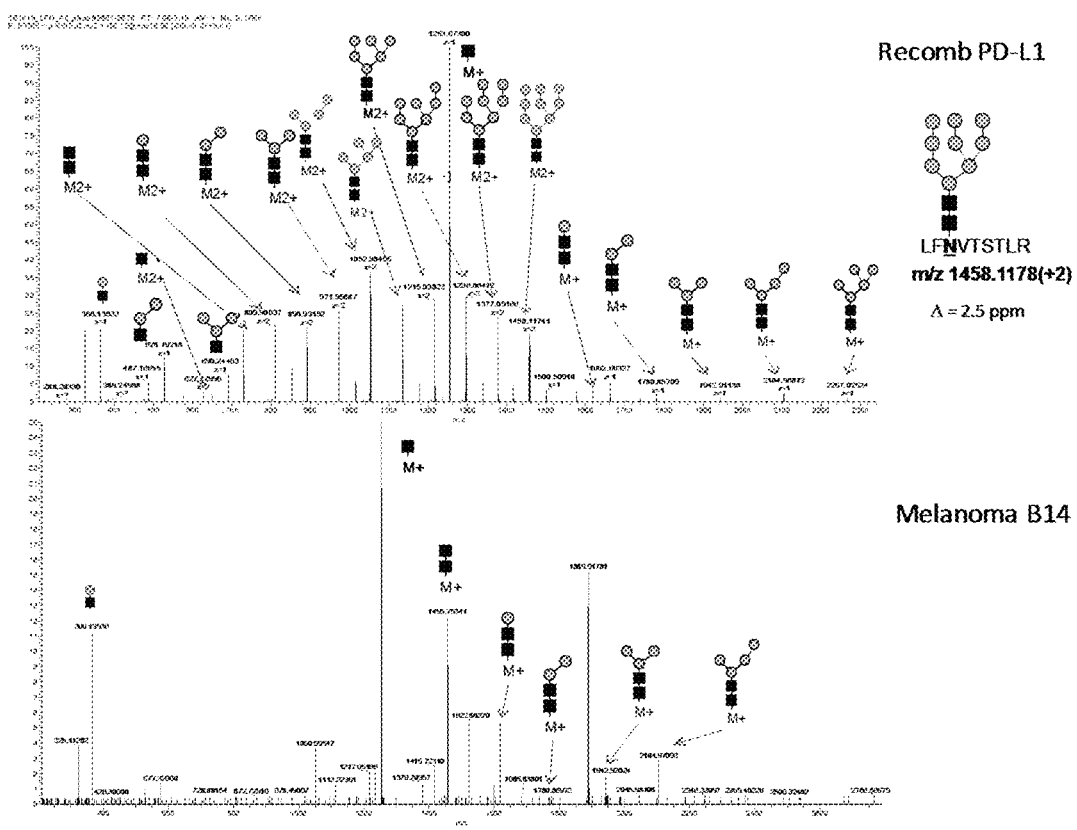

Sites of modification and glycan structures of PD-L1 N-glycosylation have not been characterized in melanomas. PD-L1 has been reported to be N-glycosylated at several residues. We first analyzed a purchased recombinant human PD-L1 containing residues 1-239 of the extracellular domain fused to the Fc region of human IgG1 at the C-terminus. Tryptic digestion of the protein, followed by treatment of the digest with PNGase-F hydrolyzed N-glycosylated peptides to sequences with aspartate residues at sites of glycosylated asparagines. This analysis identified N35, N192, and N200 as sites of N-glycosylation in the recombinant protein (FIGS. 10-12). MS/MS analysis of the tryptic N-glycopeptide forms of LFNVTSTLR, which contains the N192 residue, identified 5 glycan forms (FIGS. 13A-13E). The MS/MS spectra of putative glycopeptides contained characteristic low molecular weight oxonium ions, including m/z 204 (HexNAc+), m/z 366 (Hex-HexNAc+), and m/z 528 (Hex-Hex-HexNAc+). Candidate structures generated from the precursor ion m/z using the GlycoMod tool (http://web.expasy.org/glycomod/) were high-mannose glycans. Although these structures presented in FIGS. 13A-13E are consistent with the MS data, the number and exact identities of isomeric structures for the high mannose glycans cannot be determined from the MS data alone.

We detected these five N192-glycopeptide forms in the tryptic digests of the 22 melanomas described above (FIG. 5). MS/MS spectra matched those of five N192 glycopeptides detected in the recombinant PD-L1 protein (FIGS. 10-12). We also found that all of the glycopeptide forms eluted together in the same bRPLC fraction (Fraction 12, Table 1). This enabled us to design a relative quantitation approach in which the integrated peak areas for the highest intensity MS/MS product ion (LFN(HexNAc)VTSTLR$^+$, m/z 1253.6806) were normalized to the PD-L1 protein amounts calculated from SID measurements of the LQDAGVYR peptide in each sample.

Figure 5:
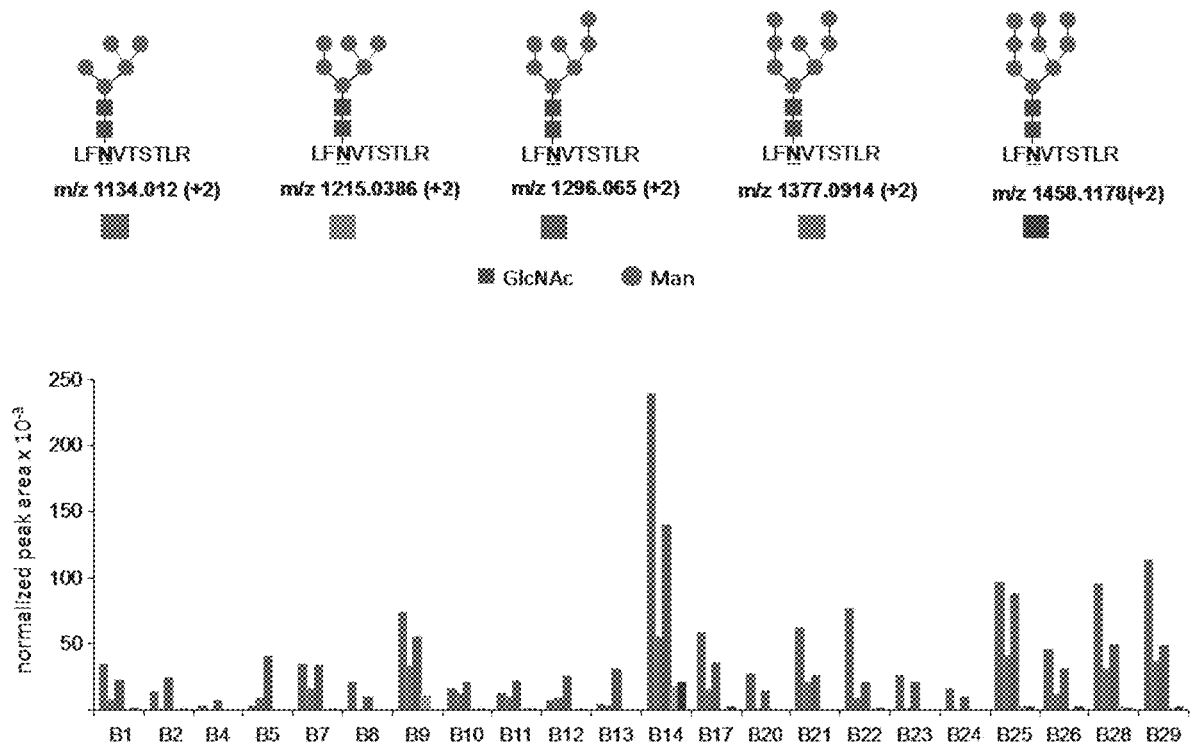
FIG. 5 shows analysis of PD-L1 N-glycosylation at position N192 in 22 melanoma samples. The upper panel depicts structures and precursor m/z for the five LFNVTSTLR (SEQ ID NO:12) glycopeptides detected in all samples. The lower panel depicts relative quantitation of the five glycopeptides, as indicated by color key. Relative quantitation was calculated from the ratio of peak area for the most abundant MS2 product ion for all glycopeptides (m/z 1253.6806), which was normalized to measured amount of PD-L1 peptide LQDAGVYR (SEQ ID NO:3) for each sample. Structures for the Man6, Man7 and Man8 glycans are representative of multiple possible positional isomers.

PD-L1 N192 glycopeptides were detectable in all of the 22 melanomas, with the Man5, Man6 and Man7 structures having the highest relative abundance (FIG. 5). The relative abundances for each glycopeptide varied approximately 50-fold. Sample B14 had the most abundantly N-glycosylated PD-L1. This sample also had the highest PD-L1 protein abundance (FIG. 2), but had very low PD-L1 positive IHC staining—only 3% of the cells in the section and no staining in tumor cells (FIG. 1, Table 3). Moreover, samples B9, B17, B21 and B28 had no IHC-detectable PD-L1 (FIG. 2), but did have MS-detectable PD-L1 (FIG. 2) and N-glycosylated PD-L1 (FIG. 5).

The unmodified N192-containing peptide LFNVTSTLR (SEQ ID NO:12) was not detected in any of the samples in the bRPLC fraction containing an isotope labeled synthetic LFNVTSTLR (SEQ ID NO:12) standard. Sample B14 had the highest degree of N192 glycosylation, together with the highest PD-L1 protein abundance, but with little detectable PD-L1 by IHC, with only 3% of the cells in the section and no staining in tumor cells (FIG. 1, Table 3). This sample was a small intestinal metastasis containing 73% tumor cells, but with PD-L1 positive IHC staining only in histiocytes, peripheral nerve and ganglion cells. The discordance between MS and IHC measurements, together with the high degree of N-glycosylation suggests that the posttranslational modification interfered with recognition by the E1L3N antibody. Samples B9, B17 and B21 also contained significant N192 PD-L1 glycosylation, but no PD-L1 was detected by IHC.

The E1L3N antibody recognizes an intracellular, C-terminal PD-L1 epitope, whereas the glycosylated residue N192 is in the PD-L1 extracellular domain. Extracellular modification thus may alter a C-terminal PD-L1 epitope. Position N192 is not contained within the PD-1 recognition sequence, which includes residues between 154 and R125 or the recognition sequence for the recently approved PD-L1 inhibitor avelumab, which includes residues between Y56 and S117. It is also not clear whether N192 glycosylation also affects recognition of PD-L1 by other antibodies used in diagnostic tests, such as the Dako 22C3 and 28-8 antibodies or would affect interaction with antibody drugs, such as atezolizumab, that are targeted to PD-L1. Tumors that test negative for PD-L1 by IHC negative may contain functionally competent PD-L1 that is significantly N-glycosylated and therefore not detectable by some antibodies. These observations may explain why patients with low levels of PD-L1 by IHC respond positively to immunotherapeutics targeting the PD1/PD-L1 interaction.

Example 6: MS Analysis of Other Immune Checkpoint and Co-Regulator Proteins

The immune-tumor interface is regulated by at least a dozen other sets of protein switches, which can modulate PD-1/PD-L1/PD-L2 mediated signaling and provide independent regulatory signals. Many of these proteins are targets for new therapeutics in preclinical development and clinical trials. This group of proteins includes IDO1, LAG3, HAVCR2 (TIM-3), VISR (VISTA, C10orf54) and CD40. IDO1 negatively regulates T-cells in the tumor microenvironment by metabolizing tryptophan to kynurenine, which suppresses T-cell activation. LAG3 and HAVCR2 (TIM-3) are T-cell receptors that mediate inhibition of T-cell activation. VISR (VISTA, C10orf54) is a V domain Ig family suppressor of T-cell activation. CD40 is an activator of cytotoxic T-cells.

Figure 6:
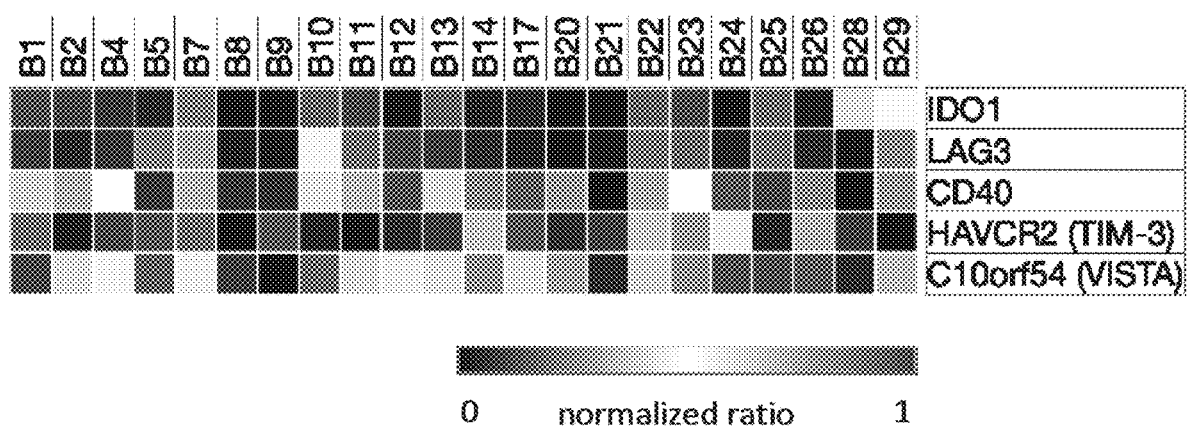
FIG. 6 shows a heatmap representation of relative quantitation of IDO1, LAG3, HAVCR2 (TIM-3), C10orf54 (VISR, VISTA) and CD40 by LRP PRM analysis of proteotypic peptides. Signals from the three most abundant PRM transitions for each target peptide were normalized to integrated signal for the three most abundant transitions for an LRP peptide present in the same bRPLC fraction.

To explore the possibility of multiplexed analysis of a broader group of protein regulators of the tumor-immune interface, PRM assays were configured for the immune checkpoint proteins IDO1, LAG3, HAVCR2 (TIM-3), VISR (VISTA, C10orf54) and CD40. A modified version of the LRP method, in which a single heavy isotope-labeled peptide is used for normalization of multiple other peptides, was used. The LRP approach does not require isotope labeled standards for quantitation, but can instead utilize other labeled peptide standards for signal normalization. Because the target peptides for all 5 proteins eluted in different bRPLC fractions, peptide signals for the five additional proteins were normalized to signals from isotope-labeled standards for PD-1, PD-L1 and PD-L2 peptides that eluted in the same bRPLC fractions (Table 1). Comparisons with the LRP method are based on ratios of the integrated transitions to those of the standard. This permits comparisons of relative amounts between samples, but not molar amounts of different proteins in the same sample. The LRP analyses detected IDO1, LAG3, TIM-3, VISTA and CD40 in the 22 melanomas (FIG. 6). Measurements revealed that IDO1, LAG3, HAVCR2 (TIM-3), VISR (VISTA, C10orf54) and CD40 all display different abundance patterns across the samples. These measurements indicated abundance differences between samples of approximately an order of magnitude for all 5 proteins. Moreover, the patterns of expression for these proteins were distinct for each and did not correlate with those for PD-1, PD-L1, and PD-L2. This suggests that these immuno-modulators function independently and that measurement of these molecules provides independent, new information about the tumor-immune interface.

Example 7: MS Analysis in Combination with IHC

Full development of a suite of several dozen SID MS assays for components of the tumor-immune interface may be envisioned. For example, the disclosed methods could be used in combination with IHC to improve accuracy of biomarker measurement. The combination of MS analyses with IHC data could overcome limitations of IHC as the sole protein biomarker measurement platform in immunotherapeutic research and diagnostics. Moreover, a targeted MS platform to analyze multiple critical immune checkpoint and co-regulator proteins could address important, unresolved issues through retrospective analyses of well-annotated, archival specimens from completed immunotherapeutics clinical trials. For example, trials of PD-1 inhibitors for melanoma reported benefit in patients who were positive and negative for PD-L1 in two different IHC tests. The results raise the question of why IHC PD-L1 negative patients responded to the drugs. The data disclosed herein suggests the following: 1) IHC failed to detect functionally competent PD-L1 due to posttranslational modification, and/or 2) expression of PD-L2 may have mediated T-cell suppression in the absence of PD-L1.

5. Exemplary Embodiments

For reasons of completeness, various aspects of the disclosure are set out in the following numbered clauses:

Clause 1: A method of quantifying PD-1 and PD-L1 in a sample, the method comprising:
(a) obtaining a biospecimen from a human subject;
(b) quantifying the levels of PD-1 and PD-L1 in the biospecimen in a combined mass spectrometry analysis.

Clause 2: The method of clause 1, wherein the levels of PD-1 and PD-L1 are quantified by targeting a PD-1 proteotypic peptide and a PD-L1 proteotypic peptide.

Clause 3: The method of clause 1, the method further comprising subjecting peptides isolated from the biospecimen to basic reverse phase liquid chromatography peptide fractionation or immunoprecipitation before performing the combined mass spectrometry analysis.

Clause 4: The method of clause 1, wherein the biospecimen is selected from the group consisting of a tissue sample; a biopsy; a formalin-fixed, paraffin-embedded tissue sample; bodily fluid; whole blood; plasma, serum; urine; bronchoalveolar lavage fluid; and a cell culture.

Clause 5: The method of any of clauses 1-4, further comprising quantifying PD-L2 in the biospecimen in the combined mass spectrometry analysis.

Clause 6: A method of quantifying PD-1 and PD-L2 in a sample, the method comprising:
(a) obtaining a biospecimen from a human subject;
(b) quantifying the levels of PD-1 and PD-L2 in the biospecimen in a combined mass spectrometry analysis.

Clause 7: The method of clause 6, wherein the levels of PD-1 and PD-L2 are quantified by targeting a PD-1 proteotypic peptide and a PD-L2 proteotypic peptide.

Clause 8: The method of clause 6, the method further comprising subjecting peptides isolated from the biospecimen to basic reverse phase liquid chromatography peptide fractionation or immunoprecipitation before performing the combined mass spectrometry analysis.

Clause 9: The method of clause 6, wherein the biospecimen is selected from the group consisting of a tissue sample; a biopsy; a formalin-fixed, paraffin-embedded tissue sample; bodily fluid; whole blood; plasma, serum; urine; bronchoalveolar lavage fluid; and a cell culture.

Clause 10: A method of quantifying the level of functionally active immune checkpoint protein in a sample, the method comprising:
(a) obtaining a biospecimen from a human subject;
(b) quantifying functionally active PD-L1 in the biospecimen by mass spectrometry targeting a PD-L1 binding site peptide;
(c) quantifying PD-L1 in the biospecimen by mass spectrometry targeting a PD-L1 core peptide.

Clause 11: The method of clause 10, wherein the PD-L1 binding site peptide and the PD-L1 core peptide are targeted in a combined mass spectrometry analysis.

Clause 12: The method of clause 10, further comprising quantifying functionally active PD-L2 in the biospecimen by mass spectrometry targeting a PD-L2 binding site peptide, and quantifying PD-L2 in the biospecimen by mass spectrometry targeting a PD-L2 core peptide.

Clause 13: The method of clause 12, wherein the PD-L1 binding site peptide, the PD-L1 core peptide, the PD-L2 binding site peptide, and the PD-L2 core peptide are targeted in a combined mass spectrometry analysis.

Clause 14: A method of quantifying the level of functionally active immune checkpoint protein in a sample, the method comprising:
(a) obtaining a biospecimen from a human subject;
(b) quantifying functionally active PD-L2 in the biospecimen by mass spectrometry targeting a PD-L2 binding site peptide;
(c) quantifying PD-L2 in the biospecimen by mass spectrometry targeting a PD-L2 core peptide.

Clause 15: The method of claim 14, wherein the PD-L2 binding site peptide and the PD-L2 core peptide are targeted in a combined mass spectrometry analysis.

Clause 16: A method of treating cancer in a subject in need thereof, the method comprising:
(a) obtaining a biospecimen from the subject;
(b) quantifying the level of functionally active PD-L1 in the biospecimen by mass spectrometry targeting a PD-L1 binding site peptide;
(c) quantifying the level of PD-L1 in the biospecimen by mass spectrometry targeting a PD-L1 core peptide; and
(d) administering an anti-PD-L1 therapeutic to the subject if the level of functionally active PD-L1 in the biospecimen is substantially equivalent to the level of PD-L1 in the biospecimen.

Clause 17: A method of treating cancer in a subject in need thereof, the method comprising:
(a) obtaining a biospecimen from the subject;
(b) quantifying the level of functionally active PD-L2 in the biospecimen by mass spectrometry targeting a PD-L2 binding site peptide;
(c) quantifying the level of PD-L2 in the biospecimen by mass spectrometry targeting a PD-L2 core peptide; and
(d) administering an anti-PD-L2 therapeutic to the subject if the level of functionally active PD-L2 in the biospecimen is substantially equivalent to the level of PD-L2 in the biospecimen.

Clause 18: A method for treating cancer in a subject in need thereof, the method comprising:
(a) obtaining a biospecimen from the subject;
(b) quantifying the levels of PD-1 and PD-L1 in the biospecimen by mass spectrometry;
(c) selecting an anticancer treatment based upon the levels of PD-1 and PD-L1 in the biospecimen; and
(d) administering the anticancer treatment to the subject.

Clause 19: A method for treating cancer in a subject in need thereof, the method comprising:
(a) obtaining a biospecimen from the subject;
(b) quantifying the levels of PD-1 and PD-L2 in the biospecimen by mass spectrometry;
(c) selecting an anticancer treatment based upon the levels of PD-1 and PD-L2 in the biospecimen; and
(d) administering the anticancer treatment to the subject.

Clause 20: A method for treating cancer in a subject in need thereof, the method comprising:
(a) obtaining a biospecimen from the subject;
(b) determining the levels of PD-1, PD-L1, and PD-L2 in the biospecimen by mass spectrometry;
(c) selecting an anticancer treatment based upon the levels of PD-1, PD-L1, and PD-L2 in the biospecimen; and
(d) administering the anticancer treatment to the subject.

Clause 21: The method of any of clauses 18-20, wherein the anticancer treatment comprises administering an anti-PD-1 antibody to the subject.

Clause 22: The method of any of clauses 18-20, wherein the anticancer treatment comprises administering an anti-PD-L1 antibody to the subject.

Clause 23: The method of any of clauses 18-20, wherein the anticancer treatment comprises administering an anti-PD-L2 antibody to the subject.

Clause 24: A method of screening a human subject for treatment with an anticancer agent, the method comprising:
(a) obtaining a biospecimen from the subject;
(b) quantifying a level of PD-1 in the biospecimen by mass spectrometry;
(c) quantifying a level of PD-L1 in the biospecimen by mass spectrometry; wherein the quantified levels of PD-1 and PD-L1 indicate responsiveness to an anti-PD-1 therapeutic if the quantified level of PD-L1 exceeds the quantified level of PD-1; and wherein the quantified levels of PD-1 and PD-L1 indicate responsiveness to an anti-PD-L1 therapeutic if the quantified level of PD-1 exceeds the quantified level of PD-L1.

Clause 25: The method of clause 24, wherein the steps of quantifying the level of PD-1 in the biospecimen and quantifying the level of PD-L1 in the biospecimen are carried out by combined mass spectrometry.

Clause 26: A method of screening a human subject for treatment with an anticancer agent, the method comprising:
(a) obtaining a biospecimen from the subject;
(b) quantifying a level of PD-1 in the biospecimen by mass spectrometry;
(c) quantifying a level of PD-L2 in the biospecimen by mass spectrometry; wherein the quantified levels of PD-1 and PD-L2 indicate responsiveness to an anti-PD-1 therapeutic if the quantified level of PD-L2 exceeds the quantified level of PD-1; and wherein the quantified levels of PD-1 and PD-L2 indicate responsiveness to an anti-PD-L2 therapeutic if the quantified level of PD-1 exceeds the quantified level of PD-L2.

Clause 27: A method of treating cancer in a subject in need thereof, the method comprising:
(a) obtaining a biospecimen from the subject;
(b) quantifying a level of PD-1 in the biospecimen by mass spectrometry;
(c) quantifying a level of PD-L1 in the biospecimen by mass spectrometry;
(d) administering an anti-PD-1 therapeutic antibody to the subject if the quantified level of PD-L1 exceeds the quantified level of PD-1.

Clause 28: The method of clause 27, wherein the steps of quantifying the level of PD-1 in the biospecimen and quantifying the level of PD-L1 in the biospecimen are carried out by combined mass spectrometry.

Clause 29: A method of treating cancer in a subject in need thereof, the method comprising:
(a) obtaining a biospecimen from the subject;
(b) quantifying a level of PD-1 in the biospecimen by mass spectrometry;
(c) quantifying a level of PD-L2 in the biospecimen by mass spectrometry;
(d) administering an anti-PD-1 therapeutic antibody to the subject if the quantified level of PD-L2 exceeds the quantified level of PD-1.

Clause 30: The method of clause 29, wherein the steps of quantifying the level of PD-1 in the biospecimen and quantifying the level of PD-L2 in the biospecimen are carried out by combined mass spectrometry.

Clause 31: A method of treating cancer in a subject in need thereof, the method comprising:
(a) obtaining a biospecimen from the subject;
(b) quantifying a level of PD-1 in the biospecimen by mass spectrometry;

(c) quantifying a level of PD-L1 in the biospecimen by mass spectrometry;
(d) administering an anti-PD-L1 therapeutic antibody to the subject if the quantified level of PD-1 exceeds the quantified level of PD-L1.

Clause 32: The method of clause 31, wherein the steps of quantifying the level of PD-1 in the biospecimen and quantifying the level of PD-L1 in the biospecimen are carried out by combined mass spectrometry.

Clause 33: A method of treating cancer in a subject in need thereof, the method comprising:
(a) obtaining a biospecimen from the subject;
(b) quantifying a level of PD-1 in the biospecimen by mass spectrometry;
(c) quantifying a level of PD-L2 in the biospecimen by mass spectrometry;
(d) administering an anti-PD-L2 therapeutic antibody to the subject if the quantified level of PD-1 exceeds the quantified level of PD-L2.

Clause 34: The method of clause 33, wherein the steps of quantifying the level of PD-1 in the biospecimen and quantifying the level of PD-L2 in the biospecimen are carried out by combined mass spectrometry.

Clause 35: A method of quantifying the level of post-translationally modified immune checkpoint protein in a sample, the method comprising:
(a) obtaining a biospecimen from a human subject;
(b) quantifying post-translationally modified PD-L1 in the biospecimen by mass spectrometry targeting a post-translationally modified PD-L1 peptide;
(c) quantifying PD-L1 in the biospecimen by mass spectrometry targeting a PD-L1 core peptide.

Clause 36: The method of clause 35, wherein the post-translationally modified PD-L1 peptide and the PD-L1 core peptide are targeted in a combined mass spectrometry analysis.

Clause 37: The method of clause 35, wherein the post-translationally modified PD-L1 peptide is glycosylated.

Clause 38: The method of clause 37, further comprising contacting the post-translationally modified PD-L1 peptide with a glycosidase.

Clause 39: The method of claim 37, wherein the glycosylated PD-L1 in the biospecimen is not recognized by an anti-PD-L1 antibody.

Clause 40: A method of treating cancer in a subject in need thereof, the method comprising:
(a) obtaining a biospecimen from a human subject;
(b) quantifying post-translationally modified PD-L1 in the biospecimen by mass spectrometry targeting a post-translationally modified PD-L1 peptide;
(c) quantifying total PD-L1 in the biospecimen by mass spectrometry targeting a PD-L1 core peptide;
(d) selecting an anticancer treatment based upon the levels of post-translationally modified PD-L1 and total PD-L1 in the biospecimen; and
(e) administering the anticancer treatment to the subject.

Clause 41: A method of treating cancer in a subject in need thereof, the method comprising:
(a) obtaining a biospecimen from a human subject;
(b) quantifying post-translationally modified PD-L1 in the biospecimen by mass spectrometry targeting a post-translationally modified PD-L1 peptide;
(c) quantifying total PD-L1 in the biospecimen by mass spectrometry targeting a PD-L1 core peptide;
(d) administering an anti-PD-1 therapeutic antibody if the quantified post-translationally modified PD-L1 in the biospecimen substantially equals the quantified total PD-L1 in the biospecimen.

Clause 42: A method of treating cancer in a subject in need thereof, the method comprising:
(a) obtaining a biospecimen from a human subject;
(b) quantifying post-translationally modified PD-L1 in the biospecimen by mass spectrometry targeting a post-translationally modified PD-L1 peptide;
(c) quantifying total PD-L1 in the biospecimen by mass spectrometry targeting a PD-L1 core peptide;
(d) administering an anti-PD-L1 therapeutic antibody if the quantified total PD-L1 in the biospecimen substantially exceeds the quantified post-translationally modified PD-L1 in the biospecimen.

Clause 43: A method of calculating an abundance ratio from a biospecimen using combined mass spectrometry analysis, the method comprising: quantifying peak area of two peptide fragments isolated from a biospecimen corresponding to at least two of programmed cell death 1 (PD-1), programmed cell death 1 ligand 1 (PD-L1), and programmed cell death 1 ligand 2 (PD-L2) using combined mass spectrometry analysis; and calculating an abundance ratio based on the quantified peak area of the two peptide fragments corresponding to the at least two PD-1, PD-L1, and PD-L2.

Clause 44: The method of clause 43, wherein the method further comprises subjecting the two peptide fragments isolated from the biospecimen to basic reverse phase liquid chromatography peptide fractionation before performing the combined mass spectrometry analysis.

Clause 45: The method of clause 43, wherein the biospecimen is selected from the group consisting of a tissue sample, a biopsy, a formalin-fixed, paraffin-embedded tissue sample, bodily fluid, whole blood, plasma, serum, urine, bronchoalveolar lavage fluid, and a cell culture.

Clause 46: The method of clause 43, wherein the two peptide fragments consist of a peptide fragment corresponding to PD-1 and a peptide fragment corresponding to PD-L1.

Clause 47: The method of clause 43, wherein the two peptide fragments consist of a peptide fragment corresponding to PD-1 and a peptide fragment corresponding to PD-L2.

Clause 48: The method of clause 43, wherein the two peptide fragments consist of a peptide fragment corresponding to PD-L1 and a peptide fragment corresponding to PD-L2.

Clause 49: The method of clause 43, wherein the two peptide fragments are selected from the group consisting of: LAAFPEDR (SEQ ID NO:6) corresponding to PD-1; VNAPYNK (SEQ ID NO:1), LQDAGVYR (SEQ ID NO:3), and LFNVTSTLR (SEQ ID NO:12) corresponding to PD-L1; and TPEGLYQVTSVLR (SEQ ID NO:9) corresponding to PD-L2.

Clause 50: The method of clause 49, wherein the two peptide fragments are glycopeptide fragments.

Clause 51: The method of clause 49, wherein the two peptide fragments are glycopeptide fragments corresponding to post-translationally modified forms of PD-1, PD-L1, and PD-L2 that are not recognized by an antibody.

Clause 52: The method of clause 49, wherein the two peptide fragments are glycopeptide fragments corresponding to PD-L1 selected from the group consisting of: LFNVTSTLR (SEQ ID NO:12), glycosylated at position N35; LFNVTSTLR (SEQ ID NO:12), glycosylated at position N192; and LFNVTSTLR (SEQ ID NO:12), glycosylated at position N200.

Clause 53: The method of clause 43, wherein the two peptide fragments comprise a binding site peptide from at least one of PD-1, PD-L1, and PD-L2, and a core peptide from at least one of PD-1, PD-L1, and PD-L2.

Clause 54: The method of clause 53, further comprising determining an amount or ratio of functionally active PD-1, PD-L1, or PD-L2 based on the quantification of the peak area of the binding site peptide from the at least one of PD-1, PD-L1, and PD-L2, and the core peptide from the at least one of PD-1, PD-L1, and PD-L2.

Clause 55: A method of treating cancer in a subject in need thereof, the method comprising: quantifying peak area of two peptide fragments isolated from a biospecimen from the subject corresponding to at least two of programmed cell death 1 (PD-1), programmed cell death 1 ligand 1 (PD-L1), and programmed cell death 1 ligand 2 (PD-L2) using combined mass spectrometry analysis; calculating an abundance ratio based on the quantified peak area of the two peptide fragments corresponding to the at least two PD-1, PD-L1, and PD-L2; and administering an anticancer agent to the subject based on the calculated abundance ratio.

Clause 56: The method of clause 55, wherein the anticancer agent comprises at least one of an anti-PD-1 antibody, an anti-PD-L1 antibody, and an anti-PD-L2 antibody.

Clause 57: The method of clause 55, wherein the anti-PD-1 antibody is administered to the subject when the calculated abundance ratio indicates levels of PD-L1 or PD-L2 exceed levels of PD-1.

Clause 58: The method of clause 55, wherein the anti-PD-L1 antibody or the anti-PD-L2 antibody is administered to the subject when the calculated abundance ratio indicates levels of PD-1 exceed levels of PD-L1.

Clause 59: The method of clause 55, wherein the anti-PD-L1 antibody or the anti-PD-L2 antibody is administered to the subject when the calculated abundance ratio indicates levels of PD-1 exceed levels of PD-L2.

Clause 60: The method of clause 55, wherein the two peptide fragments consist of a peptide fragment corresponding to PD-1 and a peptide fragment corresponding to PD-L1.

Clause 61: The method of clause 55, wherein the two peptide fragments consist of a peptide fragment corresponding to PD-1 and a peptide fragment corresponding to PD-L2.

Clause 62: The method of clause 55, wherein the two peptide fragments are selected from the group consisting of: LAAFPEDR (SEQ ID NO:6) corresponding to PD-1; VNAPYNK (SEQ ID NO:1), LQDAGVYR (SEQ ID NO:3), and LFNVTSTLR (SEQ ID NO:12) corresponding to PD-L1; and TPEGLYQVTSVLR (SEQ ID NO:9) corresponding to PD-L2.

Clause 63: The method of clause 62, wherein the two peptide fragments are glycopeptide fragments.

Clause 64: The method of clause 62, wherein the two peptide fragments are glycopeptide fragments corresponding to PD-L1 selected from the group consisting of: LFNVTSTLR (SEQ ID NO:12), glycosylated at position N35; LFNVTSTLR (SEQ ID NO:12), glycosylated at position N192; and LFNVTSTLR (SEQ ID NO:12), glycosylated at position N200.

What is claimed is:

1. A method of treating cancer in a subject in need thereof, the method comprising:
   quantifying peak area of two peptide fragments isolated from a biospecimen from the subject corresponding to at least two of programmed cell death 1 (PD-1), programmed cell death 1 ligand 1 (PD-L1), and programmed cell death 1 ligand 2 (PD-L2) using combined mass spectrometry analysis;
   calculating an abundance ratio based on the quantified peak area of the two peptide fragments corresponding to the at least two PD-1, PD-L1, and PD-L2; and
   administering an anticancer agent comprising one or more of an anti-PD-1 antibody, an anti-PD-L1 antibody, or an anti-PD-L2 antibody to the subject based on the calculated abundance ratio.

2. The method of claim 1, wherein the anti-PD-1 antibody is administered to the subject when the calculated abundance ratio indicates levels of PD-L1 or PD-L2 exceed levels of PD-1.

3. The method of claim 1, wherein the anti-PD-L1 antibody or the anti-PD-L2 antibody is administered to the subject when the calculated abundance ratio indicates levels of PD-1 exceed levels of PD-L1.

4. The method of claim 1, wherein the anti-PD-L1 antibody or the anti-PD-L2 antibody is administered to the subject when the calculated abundance ratio indicates levels of PD-1 exceed levels of PD-L2.

5. The method of claim 1, wherein the anti-PD-L1 antibody or the anti-PD-L2 antibody is administered to the subject when the calculated abundance ratio indicates levels of PD-1 exceed the combined levels of PD-L1 and PD-L2.

6. The method of claim 1, wherein the two peptide fragments consist of a peptide fragment corresponding to PD-1 and a peptide fragment corresponding to PD-L1.

7. The method of claim 1, wherein the two peptide fragments consist of a peptide fragment corresponding to PD-1 and a peptide fragment corresponding to PD-L2.

8. The method of claim 1, wherein the two peptide fragments are selected from the group consisting of:
   (a) LAAFPEDR (SEQ ID NO:6) corresponding to PD-1;
   (b) VNAPYNK (SEQ ID NO:1), LQDAGVYR (SEQ ID NO:3), and LFNVTSTLR (SEQ ID NO:12) corresponding to PD-L1; and
   (c) TPEGLYQVTSVLR (SEQ ID NO:9) corresponding to PD-L2.

9. The method of claim 8, wherein the two peptide fragments are glycopeptide fragments.

10. The method of claim 9, wherein the two peptide fragments are glycopeptide fragments corresponding to PD-L1 selected from the group consisting of:
    (a) DLYVVEYGSNMEIECK (SEQ ID NO:18), glycosylated at position N35;
    (b) LFNVTSTLR (SEQ ID NO:12), glycosylated at position N192; and
    (c) INTTTNEIFYCTFR (SEQ ID NO:16), glycosylated at position N200.

* * * * *

SEQUENCE LISTING

```
<160> NUMBER OF SEQ ID NOS: 19

<210> SEQ ID NO 1
<211> LENGTH: 7
<212> TYPE: PRT
<213> ORGANISM: Homo sapiens

<400> SEQUENCE: 1

Val Asn Ala Pro Tyr Asn Lys
1               5

<210> SEQ ID NO 2
<211> LENGTH: 6
<212> TYPE: PRT
<213> ORGANISM: Homo sapiens

<400> SEQUENCE: 2

Leu Ala Asn Asp Leu Arg
1               5

<210> SEQ ID NO 3
<211> LENGTH: 8
<212> TYPE: PRT
<213> ORGANISM: Homo sapiens

<400> SEQUENCE: 3

Leu Gln Asp Ala Gly Val Tyr Arg
1               5

<210> SEQ ID NO 4
<211> LENGTH: 8
<212> TYPE: PRT
<213> ORGANISM: Homo sapiens

<400> SEQUENCE: 4
```

Leu Pro Ala Gly Val Gly Thr Arg
1               5

<210> SEQ ID NO 5
<211> LENGTH: 7
<212> TYPE: PRT
<213> ORGANISM: Homo sapiens

<400> SEQUENCE: 5

Asp Pro Asn Leu Gly Leu Arg
1               5

<210> SEQ ID NO 6
<211> LENGTH: 8
<212> TYPE: PRT
<213> ORGANISM: Homo sapiens

<400> SEQUENCE: 6

Leu Ala Ala Phe Pro Glu Asp Arg
1               5

<210> SEQ ID NO 7
<211> LENGTH: 9
<212> TYPE: PRT
<213> ORGANISM: Homo sapiens

<400> SEQUENCE: 7

His Pro Leu Ser Tyr Val Ala Gln Arg
1               5

<210> SEQ ID NO 8
<211> LENGTH: 8
<212> TYPE: PRT
<213> ORGANISM: Homo sapiens

<400> SEQUENCE: 8

Trp Asn Leu Gly Ser Asn Ala Lys
1               5

<210> SEQ ID NO 9
<211> LENGTH: 13
<212> TYPE: PRT
<213> ORGANISM: Homo sapiens

<400> SEQUENCE: 9

Thr Pro Glu Gly Leu Tyr Gln Val Thr Ser Val Leu Arg
1               5                   10

<210> SEQ ID NO 10
<211> LENGTH: 11
<212> TYPE: PRT
<213> ORGANISM: Homo sapiens

<400> SEQUENCE: 10

Tyr Ile Leu Ile Pro Ala Ser Gln Gln Pro Lys
1               5                   10

<210> SEQ ID NO 11
<211> LENGTH: 11
<212> TYPE: PRT
<213> ORGANISM: Homo sapiens

<400> SEQUENCE: 11

Ile Leu Gly Asn Gln Gly Ser Phe Leu Thr Lys
1               5                   10

<210> SEQ ID NO 12
<211> LENGTH: 9
<212> TYPE: PRT
<213> ORGANISM: Homo sapiens

<400> SEQUENCE: 12

Leu Phe Asn Val Thr Ser Thr Leu Arg
1               5

<210> SEQ ID NO 13
<211> LENGTH: 9
<212> TYPE: PRT
<213> ORGANISM: Homo sapiens

<400> SEQUENCE: 13

Leu Phe Asp Val Thr Ser Thr Leu Arg
1               5

<210> SEQ ID NO 14
<211> LENGTH: 6
<212> TYPE: PRT
<213> ORGANISM: Homo sapiens

<400> SEQUENCE: 14

Val Thr Ser Thr Leu Arg
1               5

<210> SEQ ID NO 15
<211> LENGTH: 8
<212> TYPE: PRT
<213> ORGANISM: Homo sapiens

<400> SEQUENCE: 15

Leu Ala Asp Ala Gly Val Tyr Arg
1               5

<210> SEQ ID NO 16
<211> LENGTH: 14
<212> TYPE: PRT
<213> ORGANISM: Homo sapiens

<400> SEQUENCE: 16

Ile Asn Thr Thr Thr Asn Glu Ile Phe Tyr Cys Thr Phe Arg
1               5                   10

<210> SEQ ID NO 17
<211> LENGTH: 14
<212> TYPE: PRT
<213> ORGANISM: Homo sapiens

<400> SEQUENCE: 17

Ile Asp Thr Thr Thr Asn Glu Ile Phe Tyr Cys Thr Phe Arg
1               5                   10

<210> SEQ ID NO 18
<211> LENGTH: 16
<212> TYPE: PRT
<213> ORGANISM: Homo sapiens

<400> SEQUENCE: 18

Asp Leu Tyr Val Val Glu Tyr Gly Ser Asn Met Glu Ile Glu Cys Lys
1               5                   10                  15

```
<210> SEQ ID NO 19
<211> LENGTH: 16
<212> TYPE: PRT
<213> ORGANISM: Homo sapiens

<400> SEQUENCE: 19

Asp Leu Tyr Val Val Glu Tyr Gly Ser Asp Met Glu Ile Glu Cys Lys
1               5                   10                  15
```